(12) United States Patent
Klunk et al.

(10) Patent No.: US 7,351,401 B2
(45) Date of Patent: *Apr. 1, 2008

(54) THIOFLAVIN DERIVATIVES FOR USE IN THE ANTEMORTEM DIAGNOSIS OF ALZHEIMERS DISEASE AND IN VIVO IMAGING AND PREVENTION OF AMYLOID DEPOSITION

(75) Inventors: William E. Klunk, Pittsburgh, PA (US); Chester A. Mathis, Jr., Pittsburgh, PA (US); Yanming Wang, Imperial, PA (US)

(73) Assignee: University of Pittsburgh, Pittsburgh, PA (US)

( * ) Notice: Subject to any disclaimer, the term of this patent is extended or adjusted under 35 U.S.C. 154(b) by 592 days.

This patent is subject to a terminal disclaimer.

(21) Appl. No.: 10/859,600

(22) Filed: Jun. 3, 2004

(65) Prior Publication Data

US 2005/0043377 A1    Feb. 24, 2005

Related U.S. Application Data

(63) Continuation of application No. 09/935,767, filed on Aug. 24, 2001, now abandoned.

(60) Provisional application No. 60/227,601, filed on Aug. 24, 2000.

(51) Int. Cl.
  *A61K 51/00*  (2006.01)
  *A61M 36/14*  (2006.01)

(52) U.S. Cl. .................. 424/1.89; 424/1.11; 424/1.65; 424/1.81; 424/1.85

(58) Field of Classification Search ............... 424/1.11, 424/1.65, 1.81, 1.85, 1.89, 9.1, 9.3, 9.4, 9.5, 424/9.6, 9.7, 9.8; 548/100, 146, 215, 300.1
See application file for complete search history.

(56) References Cited

U.S. PATENT DOCUMENTS

| | | | |
|---|---|---|---|
| 3,257,204 A | 6/1966 | Süs et al. | |
| 4,500,340 A | 2/1985 | Becker et al. | |
| 4,540,648 A | 9/1985 | Scheler | |
| 5,935,927 A | 8/1999 | Vitck et al. | |
| 6,034,246 A | 3/2000 | Stevens et al. | |
| 6,696,039 B2 * | 2/2004 | Kung et al. | 424/1.89 |
| 6,858,633 B1 * | 2/2005 | Stevens et al. | 514/367 |
| 6,946,116 B2 * | 9/2005 | Kung et al. | 424/1.89 |
| 7,270,800 B2 * | 9/2007 | Klunk et al. | 424/1.89 |
| 2003/0236391 A1 | 12/2003 | Klunk et al. | |

FOREIGN PATENT DOCUMENTS

| | | |
|---|---|---|
| EP | 0 081 141 | 12/1981 |
| EP | 0 118 086 | 3/1983 |
| EP | 0 287 909 | 10/1988 |
| WO | WO 95/06469 | 3/1995 |
| WO | WO 97/26919 | 7/1997 |
| WO | WO 98/17267 | 4/1998 |
| WO | WO 01/14354 A1 | 3/2001 |
| WO | WO 02/16333 A2 | 2/2002 |
| WO | WO 02/085903 A2 | 10/2002 |

OTHER PUBLICATIONS

Shi et al., "Antitumor Benzothiazoles, 3. Synthesis of 2-(4-Aminophenyl)benzothiazoles and Evaluation of Their Activities against Breast Cancer Cell Lines in Vitro and in Vivo", *J. Med. Chem.*, 1996, pp. 3375-3384, vol. 39, The American Chemical Society.

Cuadro et al., "Styryl and Azastyryl 1,3-Benzazoles with Antihelmitic Activity", *II Farmaco*, 1992, pp. 477-488, vol. 47, No. 4.

Fokken et al., "Beitrag zur Darstellung von Verbindungen mit Amidino- bzw. Amidoximstruktur", *Pharmazie*, 1977, pp. 566-569, Pharmazie 32, H.10 (19).

Grozinger et al., Heterocyclic ethenyloxanilates as orally active antiallergic agents, *Eur. J. Med. Chem. Chim. Ther.*, 1985, pp. 487-491, vol. 20, No. 6.

Dryanska, "α-Hydroxybenzylation and Benzylidenation of the Methyl Group in 2-Methyl-1,3-benzoxazole and 2-Methyl-1,3-benzothiazole" Communications, 1976, pp. 37-38.

Vaz et al., "6-Substituted 2-(p-aminostyryl)benzothiazole derivatives", *Indian J. Chem.*, 1976, Sect. B, pp. 709-711, vol. 14B, No. 9.

Bogert et al., "Researches on Thiazoles, XVII. An Investigation of the Connection Between Constitution and Color in the Thioflavine Group", *Collection of Czechoslovak Chemical Communications*, 1931, pp. 480-498, vol. 3, The Chemical Laboratories.

Martvon et al., "2-Phenyl-6-Benzothiazolyl Isothiocyanates", *Collection Czechoslov. Chem. Commun.* 1974, pp. 1356-1365, vol. 39, No. 5.

Klunk et al., "Uncharged thioflavin-T derivatives bind to amyloid-beta protein with high affinity and readily enter the brain", *Life Sciences*, 2001, pp. 1471-1484, vol. 69, No. 13, Elsevier Pub.

Wang et al., "Synthesis and evaluation of a radioiodinated benzothiazole derivative as a radioligand for in vivo quantitation of beta-amyloid deposits in aging and Alzheimer's disease", *Journal of Labelled Compounds and Radiopharmaceuticals*, 2001, pp. S239-S241, vol. 44, No. Supp. 1.

Mathis et al., "Lipophilic 11C-labelled thioflavin-T analogues for imaging amyloid plaques in Alzheimer's disease", *Journal of Labelled Compounds and Radiopharmaceuticals*, 2001, pp. S26-S28, vol. 44, No. Supp. 1.

Zhuang et al., "Radioiodianted Styrylbenzenes and Thioflavins as Probes for Amyloid Aggregates", *Journal of Medicinal Chemistry*, vol. 44, No. 12, 2001, pp. 1905-1914.

(Continued)

*Primary Examiner*—Dameron L. Jones
(74) *Attorney, Agent, or Firm*—Foley & Lardner LLP

(57) ABSTRACT

This invention relates to novel thioflavin derivatives, methods of using the derivatives in, for example, in vivo imaging of patients having neuritic plaques, pharmaceutical compositions comprising the thioflavin derivatives and method of synthesizing the compounds. The compounds find particular use in the diagnosis and treatment of patients having diseases where accumulation of neuritic plaques are prevalent. The disease states or maladies include but are not limited to Alzheimer's Disease, familial Alzheimer's Disease, Down's Syndrome and homozygotes for the apolipoprotein E4 allele.

36 Claims, 8 Drawing Sheets

OTHER PUBLICATIONS

International Search Report, 2004.

Yanming Wang et al., "Synthesis and Evaluation of 2-(3'-Iodo-4'-aminophenyl)-6-hydroxybenzothiazole for In Vivo Quantitation of Amyloid Deposits in Alzheimer's Disease", Journal of Molecular Neuroscience, vol. 19, 2002, pp. 11-14.

Chester A. Mathis et al., "A Lipophilic Thioflavin-T Derivative for Positron Emission Tomorgraphy (PET) Imaging of Amyloid in Brain", Bioorganic & Medicinal Chemistry Letters, 12 (2002), pp. 295-298.

Chester A. Mathis et al., "Synthesis and Evaluation of [11]C-Labeled 6-Substituted 2-Arylbenzothiazoles as Amyloid Imaging Agents", J. Med. Chem., 2003, 46, pp. 2740-2754.

* cited by examiner

Proposed Structure of a Major Component of Thioflavin S (ThS)

THIOFLAVIN DERIVATIVES FOR USE IN THE ANTEMORTEM DIAGNOSIS OF ALZHEIMERS DISEASE AND IN VIVO IMAGING AND PREVENTION OF AMYLOID DEPOSITION

CROSS-REFERENCE TO RELATED PATENT APPLICATIONS

This application is a continuation of U.S. application Ser. No. 09/935,767, filed Aug. 24, 2001 now abandoned which claimed the benefit of U.S. Application 60/227,601, filed Aug. 24, 2000, incorporated herein by reference in its entirety.

FIELD OF THE INVENTION

The present invention relates to the identification of compounds that are suitable for imaging amyloid deposits in living patients. More specifically, the present invention relates to a method of imaging amyloid deposits in brain in vivo to allow antemortem diagnosis of Alzheimer's Disease. The present invention also relates to therapeutic uses for such compounds.

BACKGROUND OF THE INVENTION

Alzheimer's Disease ("AD") is a neurodegenerative illness characterized by memory loss and other cognitive deficits. McKhann et al., *Neurology* 34: 939 (1984). It is the most common cause of dementia in the United States. AD can strike persons as young as 40-50 years of age, yet, because the presence of the disease is difficult to determine without dangerous brain biopsy, the time of onset is unknown. The prevalence of AD increases with age, with estimates of the affected population reaching as high as 40-50% by ages 85-90. Evans et al., *JAMA* 262: 2551 (1989); Katzman, *Neurology* 43: 13 (1993).

In practice, AD is definitively diagnosed through examination of brain tissue, usually at autopsy. Khachaturian, *Arch. Neurol.* 42: 1097 (1985); McKhann et al., *Neurology* 34: 939 (1984). Neuropathologically, this disease is characterized by the presence of neuritic plaques (NP), neurofibrillary tangles (NFT), and neuronal loss, along with a variety of other findings. Mann, *Mech. Ageing Dev.* 31: 213 (1985). Post-mortem slices of brain tissue of victims of Alzheimer's disease exhibit the presence of amyloid in the form of proteinaceous extracellular cores of the neuritic plaques that are characteristic of AD.

The amyloid cores of these neuritic plaques are composed of a protein called the β-amyloid (Aβ) that is arranged in a predominately beta-pleated sheet configuration. Mori et al., *Journal of Biological Chemistry* 267: 17082 (1992); Kirschner et al., *PNAS* 83: 503 (1986). Neuritic plaques are an early and invariant aspect of the disease. Mann et al., *J. Neurol. Sci.* 89: 169; Mann, *Mech. Ageing Dev.* 31: 213 (1985); Terry et al., *J. Neuropathol. Exp. Neurol* 46: 262 (1987).

The initial deposition of Aβ probably occurs long before clinical symptoms are noticeable. The currently recommended "minimum microscopic criteria" for the diagnosis of AD is based on the number of neuritic plaques found in brain. Khachaturian, *Arch. Neurol.*, supra (1985). Unfortunately, assessment of neuritic plaque counts must be delayed until after death.

Amyloid-containing neuritic plaques are a prominent feature of selective areas of the brain in AD as well as Down's Syndrome and in persons homozygous for the apolipoprotein E4 allele who are very likely to develop AD. Corder et al., *Science* 261: 921 (1993); Divry, P., *J. Neurol. Psych.* 27: 643-657 (1927); Wisniewski et al., in Zimmerman, H. M. (ed.): PROGRESS IN NEUROPATHOLOGY (Grune and Stratton, N.Y. 1973) pp. 1-26. Brain amyloid is readily demonstrated by staining brain sections with thioflavin S or Congo red. Puchtler et al., *J. Histochem. Cytochem.* 10: 35 (1962). Congo red stained amyloid is characterized by a dichroic appearance, exhibiting a yellow-green polarization color. The dichroic binding is the result of the beta-pleated sheet structure of the amyloid proteins. Glenner, G. N. *Eng. J. Med.* 302: 1283 (1980). A detailed discussion of the biochemistry and histochemistry of amyloid can be found in Glenner, *N. Eng. J. Med.*, 302: 1333 (1980).

Thus far, diagnosis of AD has been achieved mostly through clinical criteria evaluation, brain biopsies and post-mortem tissue studies. Research efforts to develop methods for diagnosing Alzheimer's disease in vivo include (1) genetic testing, (2) immunoassay methods and (3) imaging techniques.

Evidence that abnormalities in Aβ metabolism are necessary and sufficient for the development of AD is based on the discovery of point mutations in the Aβ precursor protein in several rare families with an autosomal dominant form of AD. Hardy, *Nature Genetics* 1: 233 (1992); Hardy et al., *Science* 256: 184 (1992). These mutations occur near the N- and C-terminal cleavage points necessary for the generation of Aβ from its precursor protein. St. George-Hyslop et al., *Science* 235: 885 (1987); Kang et al., *Nature* 325: 733 (1987); Potter WO 92/17152. Genetic analysis of a large number of AD families has demonstrated, however, that AD is genetically heterogeneous. St. George-Hyslop et al., *Nature* 347: 194 (1990). Linkage to chromosome 21 markers is shown in only some families with early-onset AD and in no families with late-onset AD. More recently a gene on chromosome 14 whose product is predicted to contain multiple transmembrane domains and resembles an integral membrane protein has been identified by Sherrington et al., *Nature* 375: 754-760 (1995). This gene may account for up to 70% of early-onset autosomal dominant AD. Preliminary data suggests that this chromosome 14 mutation causes an increase in the production of Aβ. Scheuner et al., *Soc. Neurosci. Abstr.* 21: 1500 (1995). A mutation on a very similar gene has been identified on chromosome 1 in Volga German kindreds with early-onset AD. Levy-Lahad et al., *Science* 269: 973-977 (1995).

Screening for apolipoprotein E genotype has been suggested as an aid in the diagnosis of AD. Scott, *Nature* 366: 502 (1993); Roses, *Ann. Neurol.* 38: 6-14 (1995). Difficulties arise with this technology, however, because the apolipoprotein E4 allele is only a risk factor for AD, not a disease marker. It is absent in many AD patients and present in many non-demented elderly people. Bird, *Ann. Neurol.* 38: 2-4 (1995).

Immunoassay methods have been developed for detecting the presence of neurochemical markers in AD patients and to detect an AD related amyloid protein in cerebral spinal fluid. Warner, *Anal. Chem.* 59: 1203A (1987); World Patent No. 92/17152 by Potter; Glenner et al., U.S. Pat. No. 4,666,829. These methods for diagnosing AD have not been proven to detect AD in all patients, particularly at early stages of the disease and are relatively invasive, requiring a spinal tap. Also, attempts have been made to develop monoclonal antibodies as probes for imaging of Aβ. Majocha et al., *J. Nucl. Med.*, 33: 2184 (1992); Majocha et al., WO 89/06242 and Majocha et al., U.S. Pat. No. 5,231, 000. The major disadvantage of antibody probes is the difficulty in getting these large molecules across the blood-brain barrier. Using antibodies for in vivo diagnosis of AD would require marked abnormalities in the blood-brain barrier in order to gain access into the brain. There is no convincing functional evidence that abnormalities in the blood-brain barrier reliably exist in AD. Kalaria, *Cerebrovascular & Brain Metabolism Reviews* 4: 226 (1992).

Radiolabeled Aβ peptide has been used to label diffuse, compact and neuritic type plaques in sections of AD brain. See Maggio et al., WO 93/04194. However, these peptides share all of the disadvantages of antibodies. Specifically, peptides do not normally cross the blood-brain barrier in amounts necessary for imaging and because these probes react with diffuse plaques, they may not be specific for AD.

The inability to assess amyloid deposition in AD until after death impedes the study of this devastating illness. A method of quantifying amyloid deposition before death is needed both as a diagnostic tool in mild or clinically confusing cases as well as in monitoring the effectiveness of therapies targeted at preventing Aβ deposition. Therefore, it remains of utmost importance to develop a safe and specific method for diagnosing AD before death by imaging amyloid in brain parenchyma in vivo. Even though various attempts have been made to diagnose AD in vivo, currently, there are no antemortem probes for brain amyloid. No method has utilized a high affinity probe for amyloid that has low toxicity, can cross the blood-brain barrier, and binds more effectively to AD brain than to normal brain in order to identify AD amyloid deposits in brain before a patient's death. Thus, no in vivo method for AD diagnosis has been demonstrated to meet these criteria.

Data suggest that amyloid-binding compounds will have therapeutic potential in AD and type 2 diabetes mellitus. Morphological reactions including, reactive astrocytosis, dystrophic neurites, activated microglia cells, synapse loss, and full complement activation found around neuritic plaques all signify that neurotoxic and cell degenerative processes are occurring in the areas adjacent to these Aβ deposits. Joachim et al., *Am. J. Pathol.* 135: 309 (1989); Masliah et al., loc. cit. 137: 1293 (1990); Lue and Rogers, *Dementia* 3: 308 (1992). Aβ-induced neurotoxicity and cell degeneration has been reported in a number of cell types in vitro. Yankner et al., *Science* 250: 279 (1990); Roher et al., *BBRC* 174: 572 (1991); Frautschy et al., *Proc. Natl. Acad. Sci.* 88: 83362 (1991); Shearman et al., loc. cit. 91: 1470 (1994). It has been shown that aggregation of the Aβ peptide is necessary for in vitro neurotoxicity. Yankner, *Neurobiol. Aging* 13: 615 (1992). Recently, three laboratories have reported results which suggest that Congo red inhibits Aβ-induced neurotoxicity and cell degeneration in vitro. Burgevin et al., *NeuroReport* 5: 2429 (1994); Lorenzo and Yankner, *Proc. Natl. Acad. Sci.* 91: 12243 (1994); Pollack et al., *Neuroscience Letters* 184: 113 (1995); Pollack et al., *Neuroscience Letters* 197: 211 (1995). The mechanism appears to involve both inhibition of fibril formation and prevention of the neurotoxic properties of formed fibrils. Lorenzo and Yankner, *Proc. Natl. Acad. Sci.* 91: 12243 (1994). Congo red also has been shown to protect pancreatic islet cells from the toxicity caused by amylin. Lorenzo and Yankner, *Proc. Natl. Acad. Sci.* 91: 12243 (1994). Amylin is a fibrillar peptide similar to Aβ which accumulates in the pancreas in type 2 diabetes mellitus.

It is known in the art that certain azo dyes, such as Congo red, may be carcinogenic. Morgan et al. *Environmental Health Perspectives*, 102 (supp.) 2: 63-78, (1994). This potential carcinogenicity appears to be based largely on the fact that azo dyes are extensively metabolized to the free parent amine by intestinal bacteria. Cerniglia et al., *Biochem. Biophys. Res. Com.*, 107: 1224-1229, (1982). In the case of benzidine dyes (and many other substituted benzidines), it is the free amine which is the carcinogen. These facts have little implications for amyloid imaging studies in which an extremely minute amount of the high specific activity radiolabelled dye would be directly injected into the blood stream. In this case, the amount administered would be negligible and the dye would by-pass the intestinal bacteria.

In the case of therapeutic usage, these facts have critical importance. Release of a known carcinogen from a therapeutic compound is unacceptable. A second problem with diazo dye metabolism is that much of the administered drug is metabolized by intestinal bacteria prior to absorption. This lowered bioavailability remains a disadvantage even if the metabolites released are innocuous.

Thioflavin T is a basic dye first described as a selective amyloid dye in 1959 by Vassar and Culling (*Arch. Pathol.* 68: 487 (1959)). Schwartz et al. (*Zbl. Path.* 106: 320 (1964)) first demonstrated the use of Thioflavin S, an acidic dye, as an amyloid dye in 1964. The properties of both Thioflavin T and Thioflavin S have since been studied in detail. Kelenyi *J. Histochem. Cytochem.* 15: 172 (1967); Burns et al. *J. Path. Bact.* 94:337 (1967); Guntern et al. *Experientia* 48: 8 (1992); LeVine *Meth. Enzymol.* 309: 274 (1999). Thioflavin S is commonly used in the post-mortem study of amyloid deposition in AD brain where it has been shown to be one of the most sensitive techniques for demonstrating senile plaques. Vallet et al. *Acta Neuropathoi.* 83: 170 (1992). Thioflavin T has been frequently used as a reagent to study the aggregation of soluble amyloid proteins into beta-sheet fibrils. LeVine *Prot. Sci.* 2: 404 (1993). Quaternary amine derivatives related to Thioflavin T have been proposed as amyloid imaging agents, although no evidence of brain uptake of these agents has been presented. Caprathe et al. U.S. Pat. No. 6,001,331.

Thus, a need exists for amyloid binding compounds which enter the brain and bind selectively to amyloid.

A further need exists for amyloid binding compounds that are non-toxic and bioavailable and, consequently, can be used in therapeutics.

SUMMARY OF THE INVENTION

It is therefore one embodiment of the present invention to provide compounds which allow for a safe and specific method for diagnosing AD before death by in vivo imaging of amyloid in brain parenchyma.

It is another embodiment of the present invention to provide an approach for identifying AD amyloid deposits in brain before a patient's death, using a high-affinity probe for amyloid which has low toxicity, can cross the blood-brain barrier, and can distinguish AD brain from normal brain.

In accomplishing these and other embodiments of the invention, there is provided, in accordance with one aspect of the invention, an amyloid binding compound having one of structures A-E:

Structure A

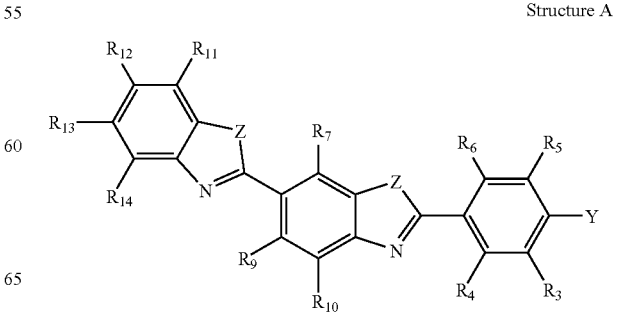

Structure B

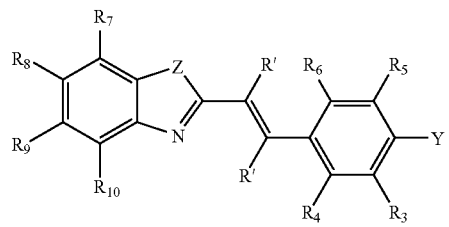

Structure C

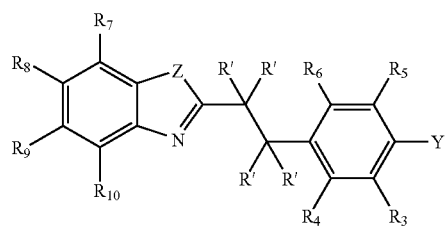

Structure D

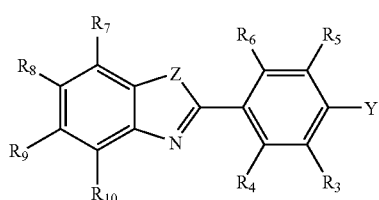

Structure E

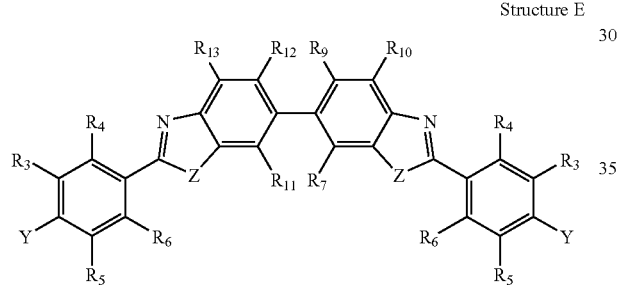

wherein Z is S, NR', O or C(R')₂ in which case the correct tautomeric form of the heterocyclic ring becomes an indole in which R' is H or a lower alkyl group:

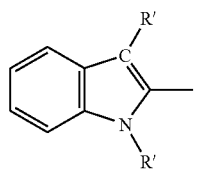

wherein Y is $NR^1R^2$, $OR^2$, or $SR^2$;

wherein the nitrogen of

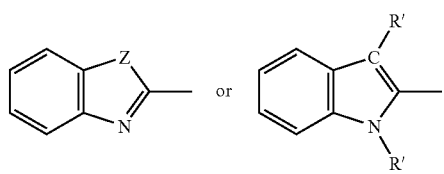

is not a quaternary amine;

or an amyloid binding compound having one of structures F-J or a water soluble, non-toxic salt thereof:

Structure F

Structure G

Structure H

Structure I

Structure J wherein each Q is independently selected from one of the following structures:

 wherein n = 0, 1, 2, 3 or 4,

-continued

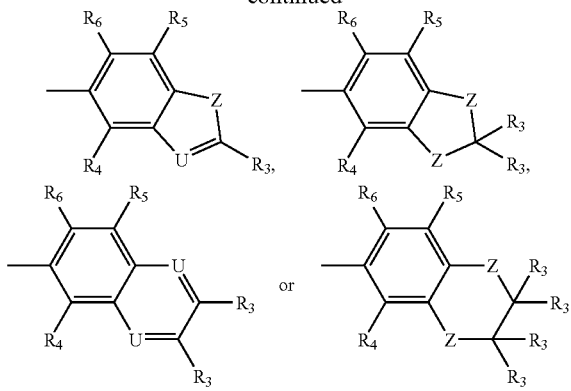

wherein Z is S, O, NR', or C(R')$_2$ in which R' is H or a lower alkyl group;

wherein U is CR' (in which R' is H or a lower alkyl group) or N (except when U=N, then Q is not

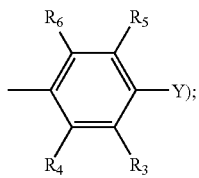

wherein Y is NR$^1$R$^2$, OR$^2$, or SR$^2$;

wherein the nitrogen of

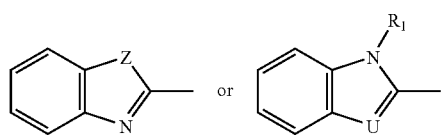

is not a quaternary amine;

wherein each R$^1$ and R$^2$ independently is selected from the group consisting of H, a lower alkyl group, (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and (CH$_2$)$_n$R$_{ph}$ (wherein n=1, 2, 3, or 4 and R$_{ph}$ represents an unsubstituted or substituted phenyl group with the phenyl substituents being chosen from any of the non-phenyl substituents defined below for R$^3$-R$^{14}$ and R' is H or a lower alkyl group); and wherein each R$^3$-R$^{14}$ independently are selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$, CR$_2$'—CR$_2$'—R$_{ph}$ (wherein R$_{ph}$ represents an unsubstituted or substituted phenyl group with the phenyl substituents being chosen from any of the non-phenyl substituents defined for R$^1$-R$^{14}$ and wherein R' is H or a lower alkyl group), a tri-alkyl tin and a chelating group (with or without a chelated metal group) of the form W-L or V-W-L, wherein V is selected from the group consisting of —COO—, —CO—, —CH$_2$O— and —CH$_2$NH—; W is —(CH$_2$)$_n$ where n=0,1,2,3,4, or 5; and L is:

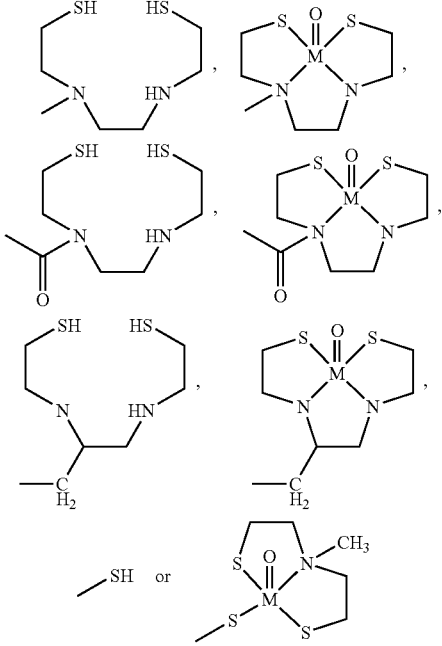

wherein M is selected from the group consisting of Tc and Re;

or wherein each R$^1$ and R$^2$ is a chelating group (with or without a chelated metal group) of the form W-L, wherein W is —(CH$_2$)$_n$ where n=2,3,4, or 5; and L is:

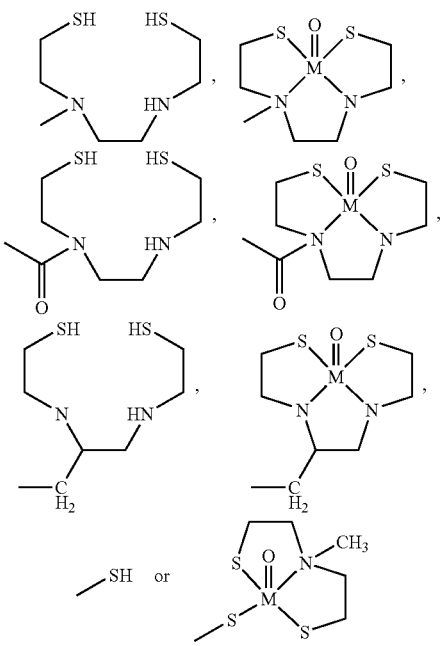

wherein M is selected from the group consisting of Tc and Re;

or wherein each $R^1$-$R^{14}$ independently is selected from the group consisting of a chelating group (with or without a chelated metal ion) of the form W-L and V-W-L, wherein V is selected from the group consisting of —COO— and —CO—; W is —$(CH_2)_n$ where n=0,1,2,3,4, or 5; L is:

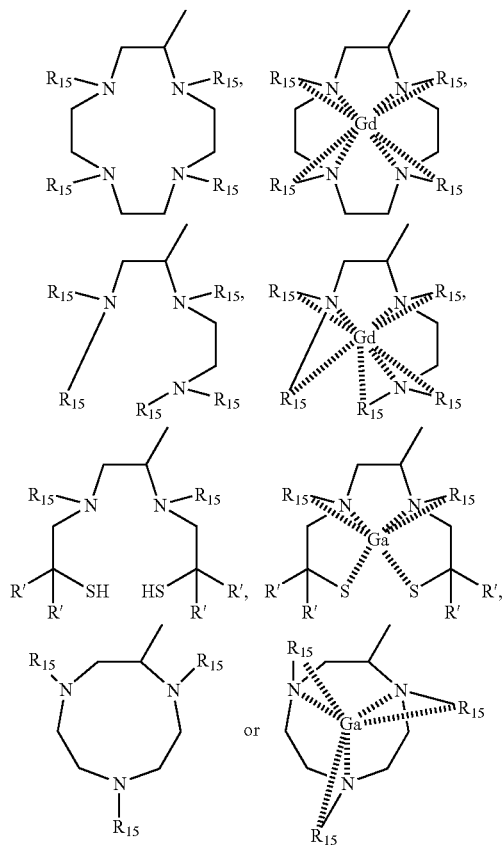

and wherein $R^{15}$ independently is selected from one of:

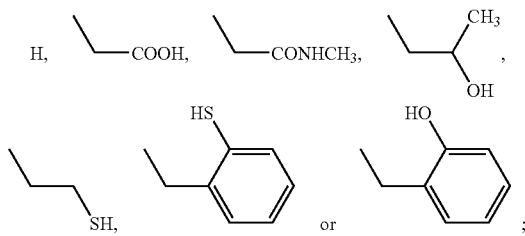

or an amyloid binding, chelating compound (with or without a chelated metal group) or a water soluble, non-toxic salt thereof of the form:

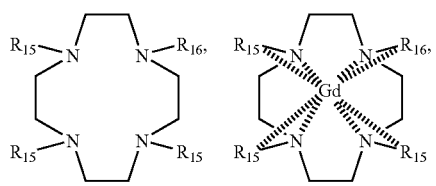

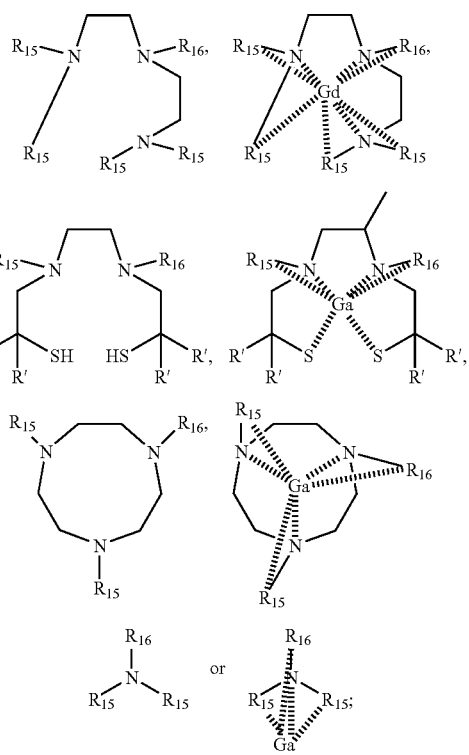

wherein $R^{15}$ independently is selected from one of:

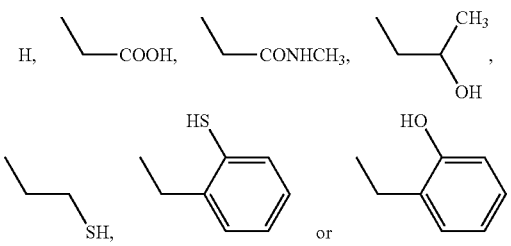

and $R^{16}$ is

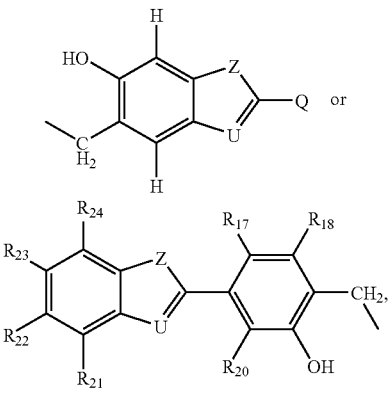

wherein Q is independently selected from one of the following structures:

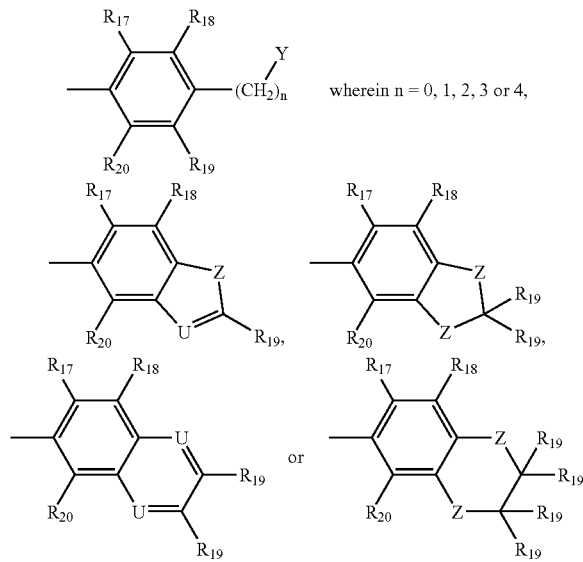

wherein Z is S, NR', O, or C(R')$_2$ in which R' is H or a lower alkyl group;

wherein U is N or CR';

wherein Y is NR$^1$R$^2$OR$^{26}$, or SR$^{26}$;

wherein each R$^{17}$-R$^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group with the phenyl substituents being chosen from any of the non-phenyl substituents defined for R$^{17}$-R$^{20}$ and wherein R' is H or a lower alkyl group).

In a preferred embodiment, at least one of the substituents R$^1$-R$^{14}$ of the structures A-E or F-J is selected from the group consisting of $^{131}$I, $^{123}$I, $^{76}$Br, $^{75}$Br, $^{18}$F, CH$_2$—CH$_2$—X*, O—CH$_2$—CH$_2$—X*, CH$_2$—CH$_2$—CH$_2$—X*, O—CH$_2$—CH$_2$—CH$_2$—X* (wherein X*=$^{131}$I, $^{123}$I, $^{76}$Br, $^{75}$Br or $^{18}$F), $^{19}$F, $^{125}$I, a carbon-containing substituent as specified above wherein at least one carbon is $^{11}$C or $^{13}$C and a chelating group (with chelated metal group) of the form W-L* or V-W-L*, wherein V is selected from the group consisting of —COO—, —CO—, —CH$_2$O— and —CH$_2$NH—; W is —(CH$_2$)$_n$ where n=0,1,2,3,4, or 5; and L* is:

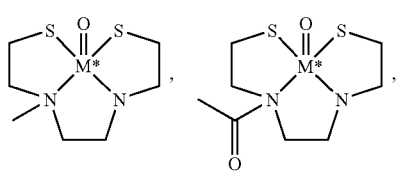

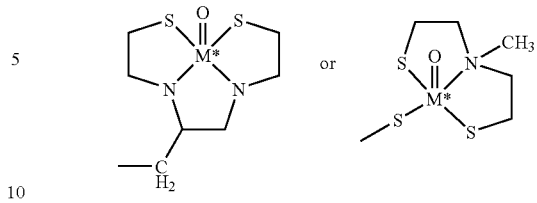

wherein M* is $^{99m}$Tc;

and a chelating group (with chelated metal group) of the form W-L* or V-W-L*, wherein V is selected from the group consisting of —COO—, —CO—, —CH$_2$O— and —CH$_2$NH—; W is —(CH$_2$)$_n$ where n=0,1,2,3,4, or 5; and L* is:

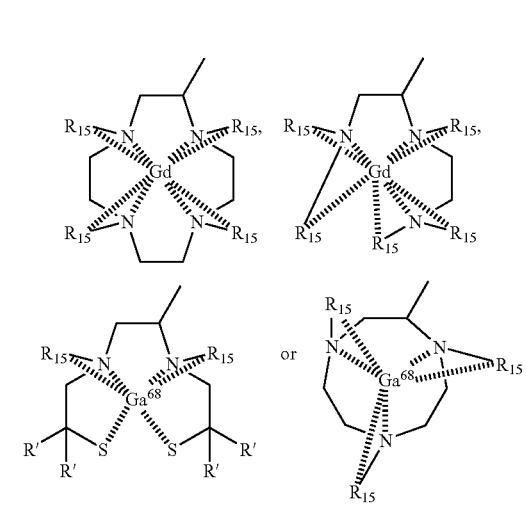

and wherein R$^{15}$ independently is selected from one of the following:

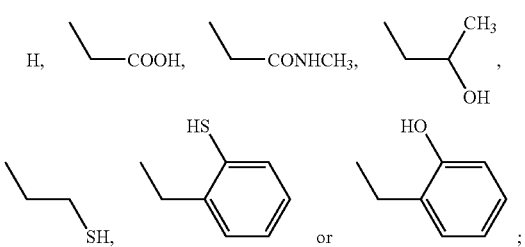

or the chelating compound (with chelated metal group) of the form:

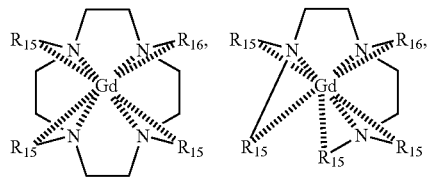

-continued

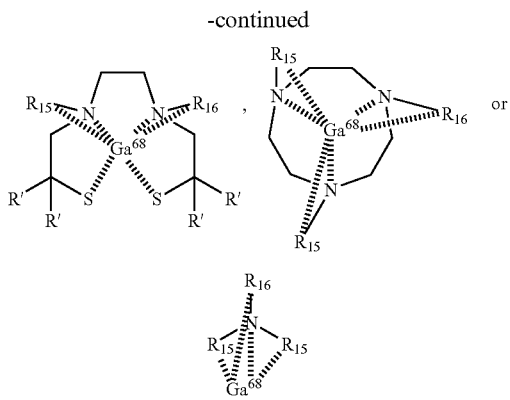

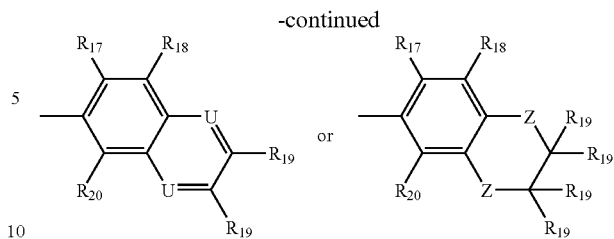

wherein R¹⁵ independently is selected from one of the following:

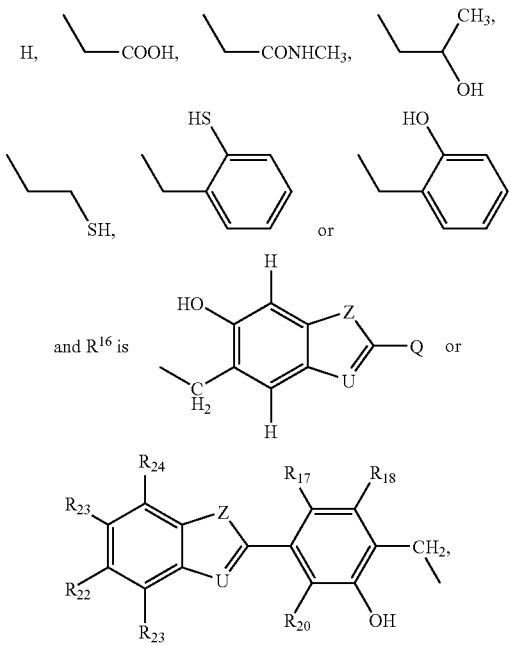

and R¹⁶ is wherein Q is independently selected from one of the following structures:

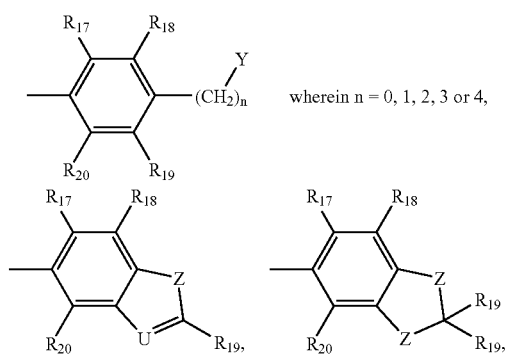

wherein Z is S, NR', O, or C(R')$_2$ in which R' is H or a lower alkyl group;

wherein U is N or CR';

wherein Y is NR¹R², OR², or SR²;

wherein each R¹⁷-R²⁴ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'R$_{ph}$ and CR$_2$'—CR$_2$'—R$_{ph}$ (wherein R$_{ph}$ represents an unsubstituted or substituted phenyl group with the phenyl substituents being chosen from any of the non-phenyl substituents defined for R¹⁷-R²⁰ and wherein R' is H or a lower alkyl group).

In another preferred embodiment, the thioflavin compounds are defined where Z=S, Y=N, R=H; and further wherein when the amyloid binding compound of the present invention is structure A or E, then R² is selected from the group consisting of a lower alkyl group, (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and (CH$_2$)$_n$R$_{ph}$ wherein n=1, 2, 3, or 4;

wherein when the amyloid binding compound of the present invention is structure B, then R² is selected from the group consisting of (CH$_2$)$_n$OR' (wherein n=1, 2, or 3, and where when R'=H or CH$_3$, n is not 1). CF$_3$, CH$_2$—CH$_2$X and CH$_2$—CH$_2$—CH$_2$X (wherein X=F, Cl, Br or I);

wherein when the amyloid binding compound of the present invention is structure C, then R² is selected from the group consisting of a lower alkyl group, (CH$_2$)$_n$OR' (wherein n=1, 2, or 3, CF$_3$), CH$_2$—CH$_2$X, CH$_2$—CH$_2$—CH$_2$X (wherein X=F, Cl, Br or I), (C=O)—H, R$_{ph}$, and (CH$_2$)$_n$R$_{ph}$ wherein n=1, 2, 3, or 4; or wherein when the amyloid binding compound of the present invention is structure D, then R² is selected from the group consisting of (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and CH$_2$R$_{ph}$ wherein when R² is (CH$_2$)$_n$R$_{ph}$ R⁸ is not CH$_3$.

In another preferred embodiment, at least one of the substituents R³-R¹⁴ of the amyloid binding compound of the present invention is selected from the group consisting of $^{131}$I, $^{123}$I, $^{76}$Br, $^{75}$Br, $^{18}$F, CH$_2$—CH$_2$—X*, O—CH$_2$—CH$_2$—X*, CH$_2$—CH$_2$—CH$_2$—X*, O—CH$_2$—CH$_2$—CH$_2$—X* (wherein X*=$^{131}$I, $^{123}$I, $^{76}$Br, $^{75}$Br or $^{18}$F), $^{19}$F, $^{125}$I and a carbon-containing substituent as specified in the definition of the compounds having one of the structures A-E or F-J, wherein at least one carbon is $^{11}$C or $^{13}$C, a chelating group (with chelated metal group) of the form W-L* or V-W-L*, wherein V is selected from the group consisting of —COO—, —CO—, —CH$_2$O— and —CH$_2$NH—; W is —(CH$_2$)$_n$ where n=0,1,2,3,4, or 5; and L* is:

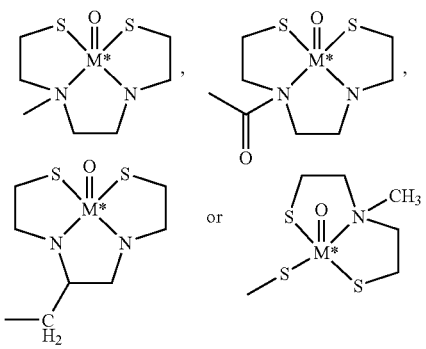

wherein M* is $^{99m}$Tc;

and a chelating group (with chelated metal group) of the form W-L* or V-W-L*, wherein V is selected from the group consisting of —COO—, —CO—, —CH$_2$O— and —CH$_2$NH—; W is —(CH$_2$)$_n$ where n=0,1,2,3,4, or 5; and L* is:

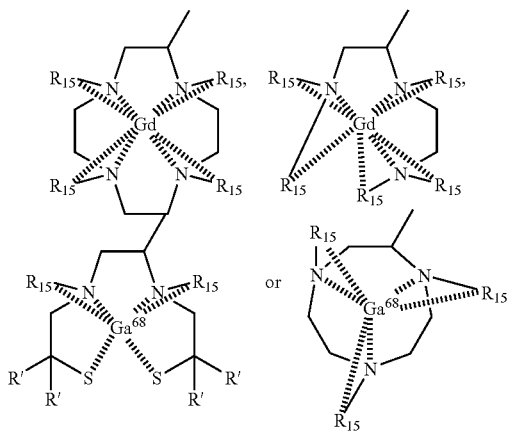

and wherein R$^{15}$ independently is selected from one of the following:

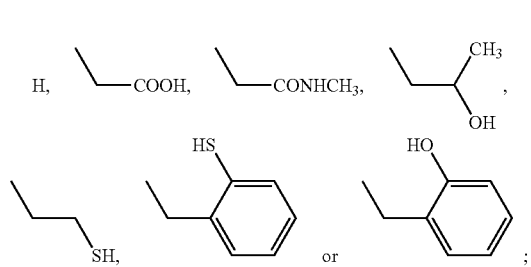

or the chelating compound (with chelated metal group) of the form:

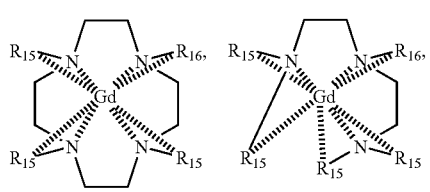 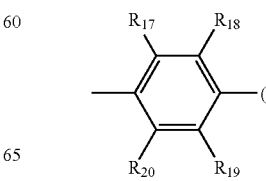

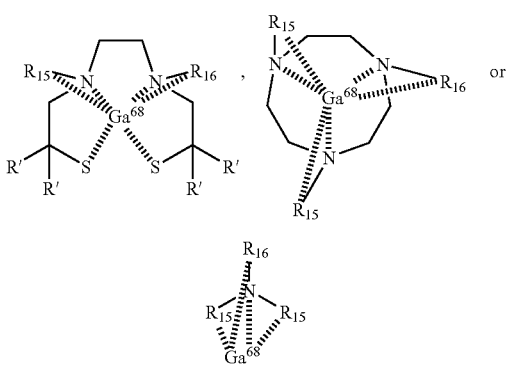

wherein R$^{15}$ independently is selected from one of the following:

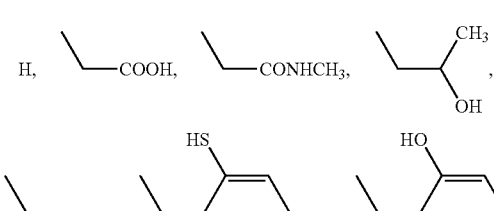

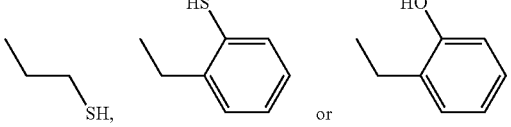

and R$^{16}$ is

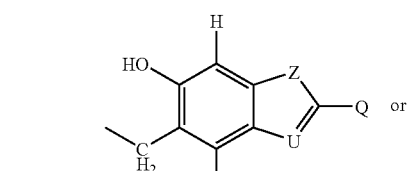

wherein Q is independently selected from one of the following structures:

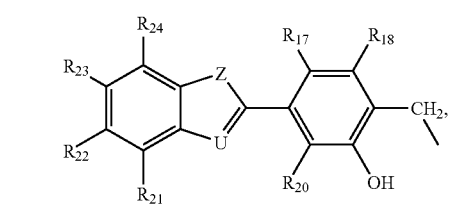

wherein n = 0, 1, 2, 3 or 4,

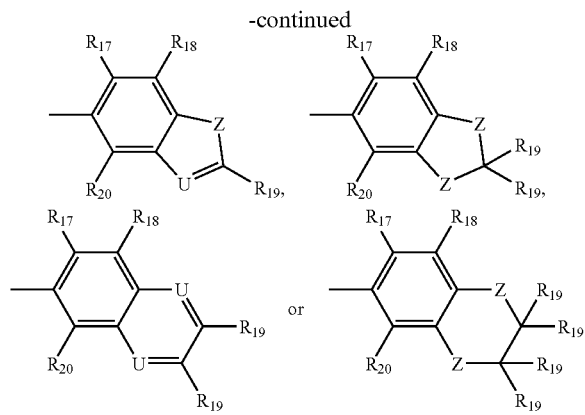

wherein Z is S, NR', O, or C(R')$_2$ in which R' is H or a lower alkyl group;

wherein U is N or CR';

wherein Y is NR$^1$R$^2$, OR$^2$, or SR$^2$;

wherein each R$^{17}$-R$^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group with the phenyl substituents being chosen from any of the non-phenyl substituents defined for R$^{17}$-R$^{20}$ and wherein R' is H or a lower alkyl group).

In especially preferred embodiments, the compound is selected from structures A-E, and Z=S, Y=N, R'=H, R$^1$=H, R$^2$=CH$_3$ and R$^3$-R$^{14}$ are H; Z=S, Y=O, R'=H, R$_2$=CH$_3$ and R$^3$-R$^{14}$ are H; Z=S, Y=N, R'=H, R$^{1-4}$=H, R$^5$=I, and R$^6$-R$^{14}$ are H; Z=S, Y=N, R'=H, R$^{1-4}$=H, R$^5$=I, R$^8$=OH and R$^6$-R$^7$ and R$^9$-R$^{14}$ are H; Z=S, Y=N, R'=H, R$^1$=H, R$^2$=CH$_2$—CH$_2$—CH$_2$—F and R$^3$-R$^{14}$ are H; Z=S, Y=O, R'=H, R$^2$=CH$_2$—CH$_2$—F and R$^3$—R$^{14}$ are H; Z=S, Y=N, R'=H, R$^{1-7}$=H, R$^8$=O—CH$_2$—CH$_2$—F and R$^9$-R$^{14}$ are H; or Z=S, Y=N, R'=H, R$^1$=CH$_3$, R$^{2-7}$=H, R$_8$=O—CH$_2$—CH$_2$—F and R$^9$-R$^{14}$ are H.

In especially preferred embodiments, the compound is selected from structures F-J, and Z=S, Y=N, R'=H, R$^1$=H, R$^2$=CH$_3$ and R$^3$-R$^{14}$ are H; Z=S, Y=O, R'=H, R$_2$=CH$_3$ and R$^3$-R$^{14}$ are H; Z=S, Y=N, R'=H, R$^{1-4}$=H, R$^5$=I, and R$^6$-R$^{14}$ are H; Z=S, Y=N, R'=H, R$_{1-4}$=H, R$^5$=I, R$^8$=OH and R$_6$-R$^7$ and R$^9$-R$^{14}$ are H; Z=S, Y=N, R'=H, R$^1$=H, R$^2$=CH$_2$—CH$_2$—F and R$^3$-R$^{14}$ are H; Z=S, Y=O, R'=H, R$^2$=CH$_2$—CH$_2$—F and R$^3$-R$^{14}$ are H; Z=S, Y=N, R'=H, R$^{1-7}$=H, R$^8$=O—CH$_2$—CH$_2$—F and R$^9$-R$^{14}$ are H; or Z=S, Y=N, R'=H, R$^1$=CH$_3$, R$^{2-7}$=H, R$^8$=O—CH$_2$—CH$_2$—F and R$^9$-R$^{14}$ are H.

In another preferred embodiment, at least one of the substituents R$^3$-R$^{14}$ is selected from the group consisting of CN, OCH$_3$, OH and NH$_2$.

In still another preferred embodiment, the amyloid binding compound is selected from the group consisting of structure B, structure C and structure D; wherein R$^1$=H, R$_2$=CH$_3$ and R$^8$ is selected from the group consisting of CN, CH$_3$, OH, OCH$_3$ and NH$_2$, in a preferred aspect of this embodiment, R$^3$-R$^7$ and R$^9$-R$^{14}$ are H.

In still another embodiment, the amyloid binding compounds of the present invention bind to Aβ with a dissociation constant (K$_D$) between 0.0001 and 10.0 μM when measured by binding to synthetic Aβ peptide or Alzheimer's Disease brain tissue.

Another embodiment of the invention relates to a method for synthesizing the amyloid binding compounds of the present invention having at least one of the substituents R$^1$-R$^{14}$ selected from the group consisting of $^{131}$I, $^{125}$I, $^{123}$I, $^{76}$Br, $^{75}$Br, $^{18}$F, and $^{19}$F, comprising the step of labeling the amyloid binding compound wherein at least one of the substituents R$^1$-R$^{14}$ is a tri-alkyl tin, by reaction of the compound with a $^{131}$I, $^{125}$I, $^{123}$I, $^{76}$Br, $^{75}$Br, $^{18}$F, or $^{19}$F containing substance.

Another embodiment of the invention relates to a method for synthesizing the amyloid binding compounds of the present invention having at least one of the substituents R$^3$-R$^{14}$ selected from the group consisting of $^{131}$I, $^{125}$I, $^{123}$I, $^{76}$Br, $^{75}$Br, $^{18}$F, and $^{19}$F, comprising the step of labeling the amyloid binding compound of structure A-E or F-J wherein Z=S, Y=N, R$^1$=H and at least one of the substituents R$^3$-R$^{14}$ is a tri-alkyl tin, by reaction of the compound with a $^{131}$I, $^{125}$I, $^{123}$I, $^{76}$Br, $^{75}$Br, $^{18}$F, or $^{19}$F containing substance.

A further embodiment of the present invention relates to a pharmaceutical composition for in vivo imaging of amyloid deposits, comprising (a) an amyloid binding compound chosen from the structures A-E or F-J, and (b) a pharmaceutically acceptable carrier. A preferred aspect of the embodiment relates to a pharmaceutical composition for in vivo imaging of amyloid deposits, comprising (a) an amyloid binding compound chosen from the structures A-E or F-J wherein Z=S, Y=N, R$^1$=H, and (b) a pharmaceutically acceptable carrier.

In another embodiment of the invention is an in vivo method for detecting amyloid deposits in a subject, comprising the steps of: (a) administering a detectable quantity of a pharmaceutical composition comprising the labeled amyloid binding compound, and detecting the binding of the compound to amyloid deposit in the subject. In a preferred aspect of this embodiment, the amyloid deposit is located in the brain of a subject. In a particularly preferred aspect of this embodiment, the subject is suspected of having a disease or syndrome selected from the group consisting of Alzheimer's Disease, familial Alzheimer's Disease, Down's Syndrome and homozygotes for the apolipoprotein E4 allele. In another particularly preferred aspect of this embodiment, the detecting is selected from the group consisting of gamma imaging, magnetic resonance imaging and magnetic resonance spectroscopy. In a preferred aspect of this embodiment, the gamma imaging is either PET or SPECT. In another preferred aspect of this embodiment, the pharmaceutical composition is administered by intravenous injection. In another preferred aspect of this embodiment, the ratio of (i) binding of the compound to a brain area other than the cerebellum to (ii) binding of the compound to the cerebellum, in a subject is compared to the ratio in a normal subject.

Another embodiment relates to a method of detecting amyloid deposits in biopsy or post-mortem human or animal tissue comprising the steps of: (a) incubating formalin-fixed or fresh-frozen tissue with a solution of an amyloid binding compound of the present invention to form a labeled deposit and then, (b) detecting the labeled deposits. In a preferred aspect of this embodiment, the solution is composed of 25-100% ethanol, with the remainder of the solution being water, wherein the solution is saturated with an amyloid binding compound according to the present invention. In a particularly preferred aspect of this embodiment, the solution is composed of an aqueous buffer (such as tris or phosphate) containing 0-50% ethanol, wherein the solution contains 0.0001 to 100 μM of an amyloid binding compound according to the present invention. In a particularly preferred aspect of this embodiment, the detecting is effected by microscopic techniques selected from the group consisting of bright-field, fluorescence, laser-confocal, and cross-polarization microscopy.

A further embodiment relates to a method of quantifying the amount of amyloid in biopsy or post-mortem tissue comprising the steps of: a) incubating a radiolabeled derivative of an amyloid binding compound of the present invention with a homogenate of biopsy or post-mortem tissue, wherein at least one of the substituents $R^1$-$R^{14}$ of the compound is labeled with a radiolabel selected from the group consisting of $^{125}I$, $^3H$, and a carbon-containing substituent as specified by the amyloid binding compound structures A-E or F-J, wherein at least one carbon is $^{14}C$, b) separating the tissue-bound from the tissue-unbound radiolabeled derivative of an amyloid binding compound of the present invention, c) quantifying the tissue-bound radiolabeled derivative of an amyloid binding compound of the present invention, and d) converting the units of tissue-bound radiolabeled derivative of an amyloid binding compound of the present invention to units of micrograms of amyloid per 100 mg of tissue by comparison with a standard.

In a preferred aspect of the above embodiment, the radiolabeled derivative of the amyloid binding compound of the present invention or a water soluble, non-toxic salt thereof is according to one of the formulae A-E below:

Structure A

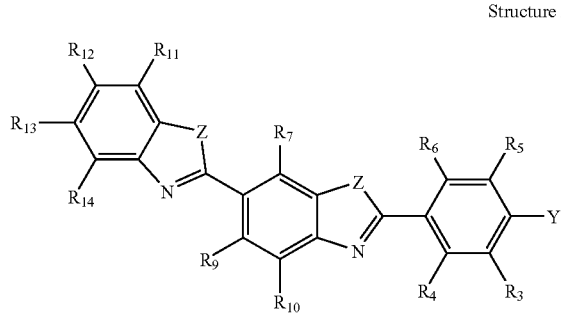

Structure B

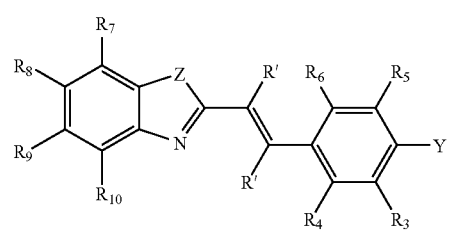

Structure C

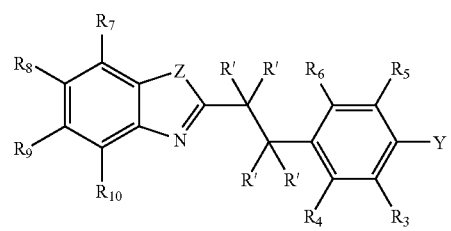

Structure D

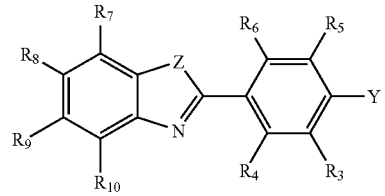

-continued

Structure E

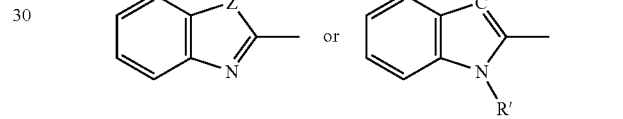

wherein Z is S, NR', O or C(R')$_2$ in which case the correct tautomeric form of the heterocyclic ring becomes an indole in which R' is H or a lower alkyl group:

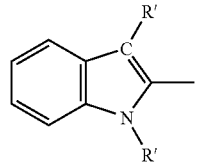

wherein Y is NR$^1$R$^2$, OR$^2$, or SR$^2$; wherein the nitrogen of any

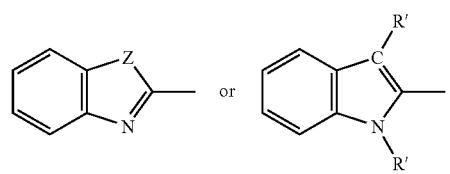

group is not a quaternary amine;

or the radiolabeled derivative of the amyloid binding compound of the present invention or a water soluble, non-toxic salt thereof is according to one of the formulae F-J below:

or

Structure F

Structure G

Structure H

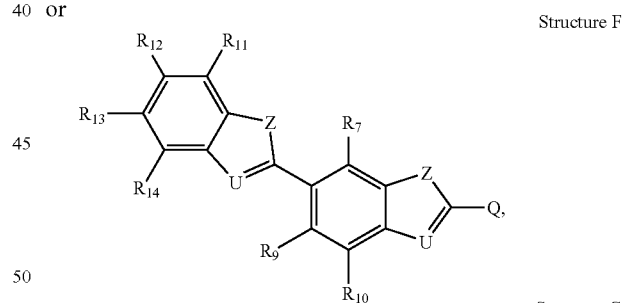

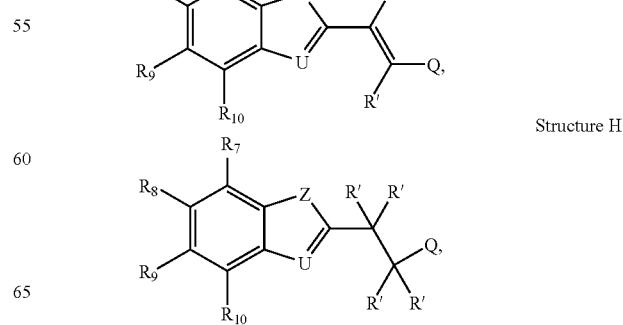

-continued

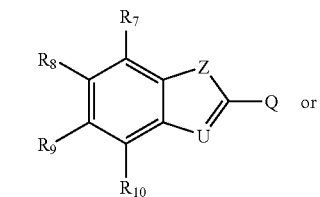
Structure I

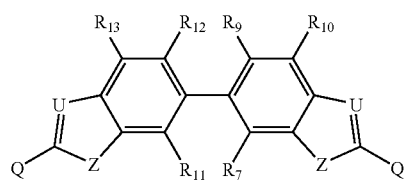
Structure J wherein each Q is independently selected from one of the following structures:

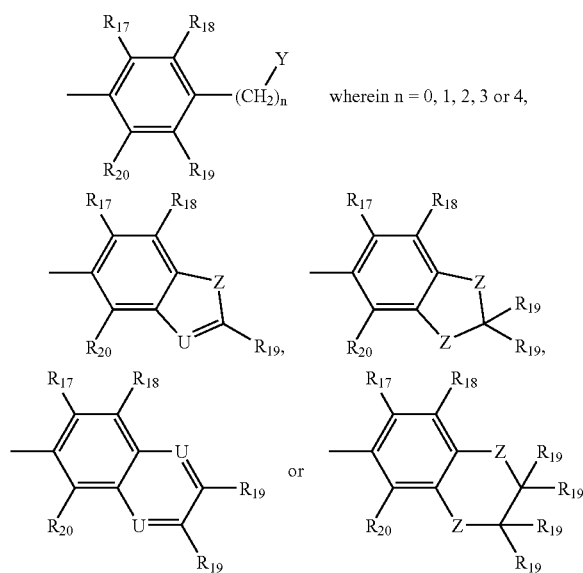

wherein Z is S, NR', O, or C(R')$_2$ in which R' is H or a lower alkyl group;

wherein U is CR' (in which R' is H or a lower alkyl group) or N (except when U=N, then Q is not

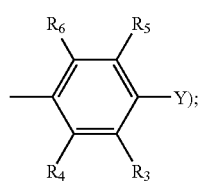

wherein Y is NR$^1$R$^2$, OR$^2$, or SR$^2$;

wherein the nitrogen of

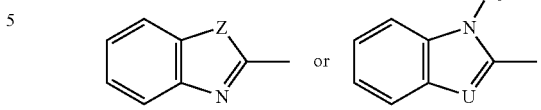

is not a quaternary amine;

wherein each R$_1$ and R$^2$ independently is selected from the group consisting of H, a lower alkyl group, (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and (CH$_2$)$_n$R$_{ph}$ (wherein n=1, 2, 3, or 4 and R$_{ph}$ represents an unsubstituted or substituted phenyl group with the phenyl substituents being chosen from any of the non-phenyl substituents defined below for R$^3$-R$^{14}$ and R' is H or a lower alkyl group); and wherein each R$^3$-R$^{14}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$-CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$, CR$_2$'—CR$_2$'—R$_{ph}$ (wherein R$_{ph}$ represents an unsubstituted or substituted phenyl group with the phenyl substituents being chosen from any of the non-phenyl substituents defined for R$^1$-R$^{14}$ and wherein R' is H or a lower alkyl group), a tri-alkyl tin and a chelating group (with or without a chelated metal group) of the form W-L or V-W-L, wherein V is selected from the group consisting of —COO—, —CO—, —CH$_2$O— and —CH$_2$NH—; W is —(CH$_2$)$_n$ where n=0,1,2,3,4, or 5; and L is:

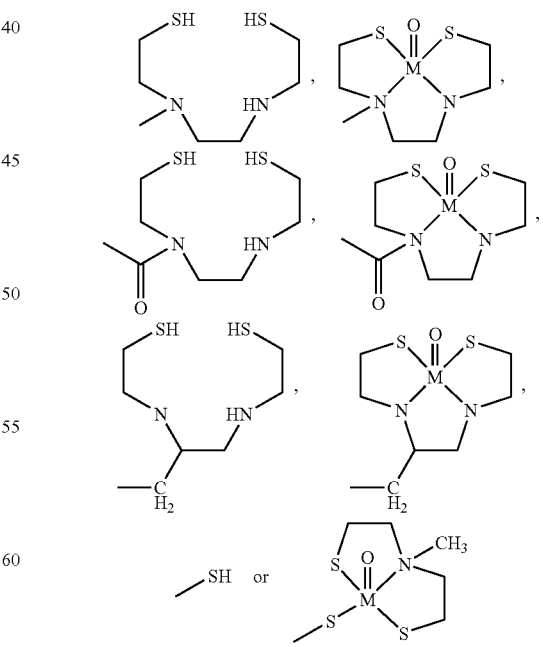

wherein M is selected from the group consisting of Tc and Re;

or wherein each $R^1$ and $R^2$ is a chelating group (with or without a chelated metal group) of the form W-L, wherein W is $-(CH_2)_n$ where n=2,3,4, or 5; and L is:

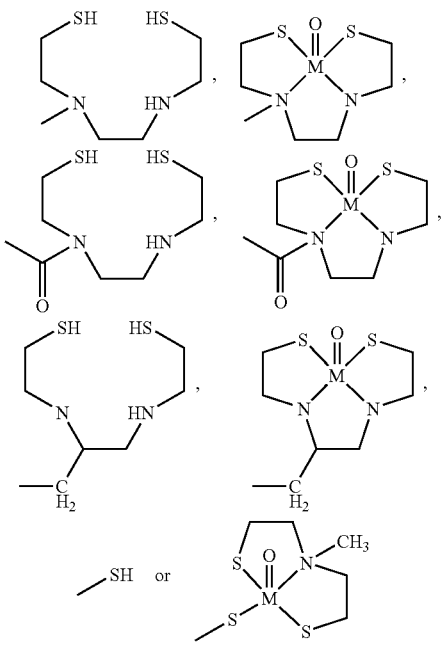

wherein M is selected from the group consisting of Tc and Re;

or wherein each $R^1$-$R^{14}$ independently is selected from the group consisting of a chelating group (with or without a chelated metal ion) of the form W-L and V-W-L, wherein V is selected from the group consisting of —COO— and —CO—; W is $-(CH_2)_n$ where n=0,1,2,3,4, or 5; L is:

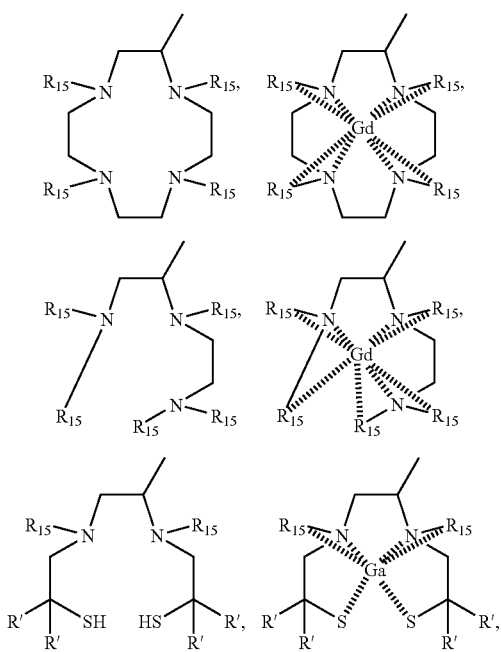

-continued

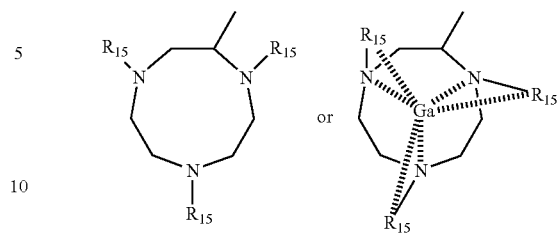

and wherein $R^{15}$ independently is selected from one of the following:

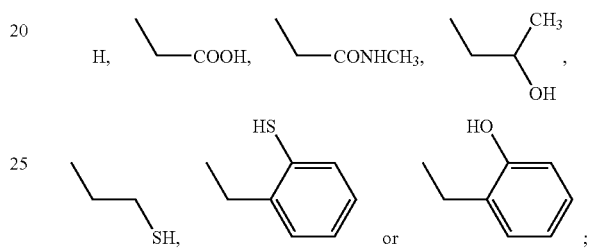

or an amyloid binding, chelating compound (with or without a chelated metal group) or a water soluble, non-toxic salt thereof of the form:

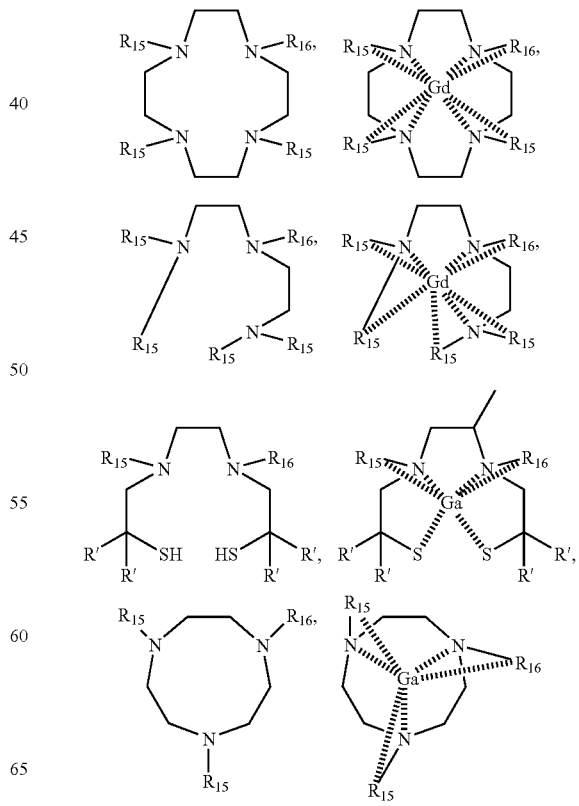

-continued

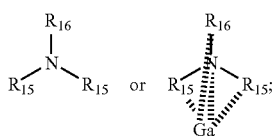

wherein $R^{15}$ independently is selected from the following:

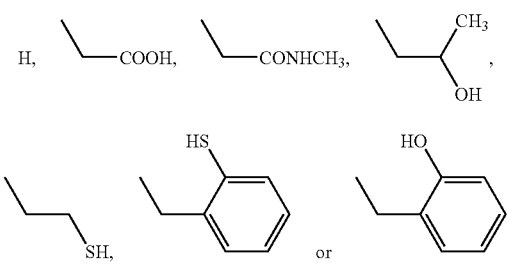

and $R^{16}$ is

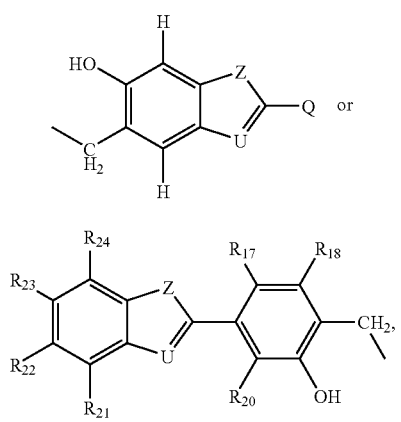

wherein Q is independently selected from one of the following structures:

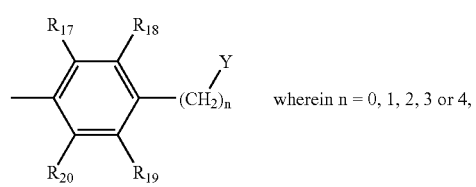 wherein n = 0, 1, 2, 3 or 4,

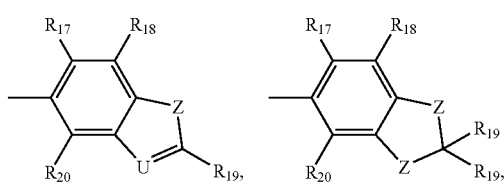

-continued

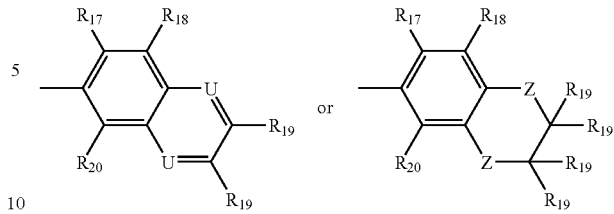

wherein Z is S, NR', O, or C(R')$_2$ in which R' is H or a lower alkyl group;

wherein U is N or CR';

wherein Y is NR$^1$R$^2$, OR$^2$, or SR$^2$;

wherein each $R^{17}$-$R^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group with the phenyl substituents being chosen from any of the non-phenyl substituents defined for $R^{17}$-$R^{20}$ and wherein R' is H or a lower alkyl group).

Another embodiment relates to a method of distinguishing an Alzheimer's disease brain from a normal brain comprising the steps of: a) obtaining tissue from (i) the cerebellum and (ii) another area of the same brain other than the cerebellum, from normal subjects and from subjects suspected of having Alzheimer's disease; b) incubating the tissues with a radiolabeled derivative of a thioflavin amyloid binding compound according to the present invention so that amyloid in the tissue binds with the radiolabeled derivative of an amyloid binding compound of the present invention; c) quantifying the amount of amyloid bound to the radiolabeled derivative of an amyloid binding compound of the present invention according to the above recited method; d) calculating the ratio of the amount of amyloid in the area of the brain other than the cerebellum to the amount of amyloid in the cerebellum; e) comparing the ratio for amount of amyloid in the tissue from normal subjects with ratio for amount of amyloid in tissue from subjects suspected of having Alzheimer's disease; and f) determining the presence of Alzheimer's disease if the ratio from the brain of a subject suspected of having Alzheimer's disease is above 90% of the ratios obtained from the brains of normal subjects.

Other embodiments of the invention will be apparent to those skilled in the art from consideration of the specification and practice of the invention disclosed herein. It is intended that the specification be considered as exemplary only, with the true scope and spirit of the invention being indicated by the following claims. Additionally, all documents referred to herein are expressly incorporated by reference.

DETAILED DESCRIPTION OF THE INVENTION

Figure 1:
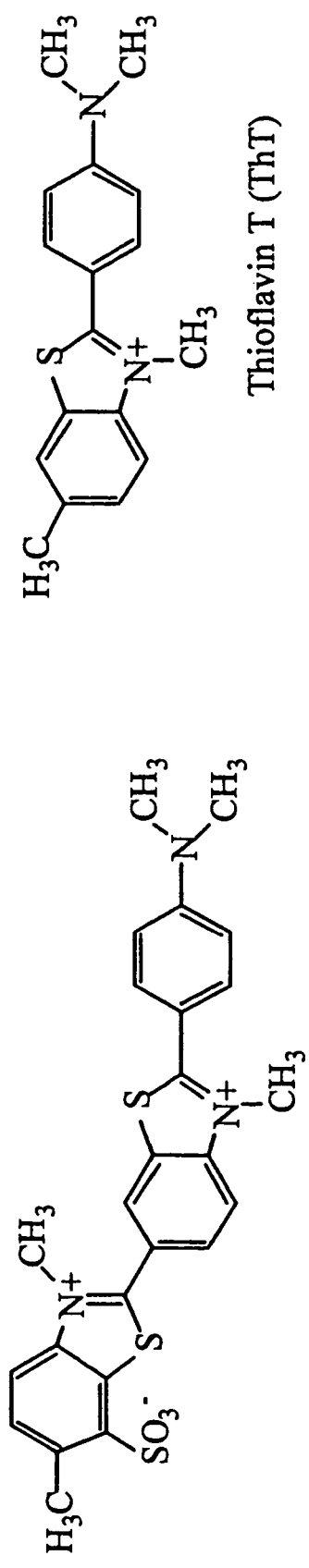
FIG. 1 Shows the structures of a Thioflavin S and Thioflavin T.

The present invention exploits the ability of Thioflavin compounds and radiolabeled derivatives thereof to cross the blood brain barrier in vivo and bind to Aβ deposited in neuritic (but not diffuse) plaques, to Aβ deposited in cerebrovascular amyloid, and to the amyloid consisting of the protein deposited in NFT. The present compounds are non-quaternary amine derivatives of Thioflavin S and T which are known to stain amyloid in tissue sections and bind to synthetic Aβ in vitro. Kelenyi *J. Histochem. Cytochem.* 15: 172 (1967); Burns et al. *J. Path. Bact.* 94:337 (1967); Guntern et al. *Experientia* 48: 8 (1992); LeVine *Meth. Enzymol.* 309: 274 (1999).

The thioflavin derivatives of the present invention have each of the following characteristics: (1) specific binding to synthetic Aβ in vitro and (2) ability to cross a non-compromised blood brain barrier in vivo.

As used herein to describe the thioflavin derivatives, "lower alkyl" is branched or straight chain $C_1$-$C_8$, preferably $C_1$-$C_6$ and most preferably $C_1$-$C_4$ (e.g., methyl, ethyl, propyl or butyl). When $R^1$-$R^{14}$ is defined as "tri-alkyl tin", the moiety is a tri-$C_1$-$C_8$ alkyl Sn moiety, preferably tri-$C_1$-$C_6$ alkyl Sn moiety, most preferably tri-$C_1$-$C_4$ alkyl Sn moiety (e.g., methyl, ethyl, propyl or butyl).

The method of this invention determines the presence and location of amyloid deposits in an organ or body area, preferably brain, of a patient. The present method comprises administration of a detectable quantity of a pharmaceutical composition containing an amyloid binding compound chosen from structures A-E or F-J, as defined above, called a "detectable compound," or a pharmaceutically acceptable water-soluble salt thereof, to a patient. A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid probes which, in conjunction with non-invasive neuroimaging techniques such as magnetic resonance spectroscopy (MRS) or imaging (MRI), or gamma imaging such as positron emission tomography (PET) or single-photon emission computed tomography (SPECT), are used to quantify amyloid deposition in vivo. The term "in vivo imaging" refers to any method which permits the detection of a labeled thioflavin derivative which is chosen from structures A-E or F-J, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having dementia.

For purposes of in vivo imaging, the type of detection instrument available is a major factor in selecting a given label. For instance, radioactive isotopes and $^{19}$F are particularly suitable for in vivo imaging in the methods of the present invention. The type of instrument used will guide the selection of the radionuclide or stable isotope. For instance, the radionuclide chosen must have a type of decay detectable by a given type of instrument. Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range. For PET detection, the radiolabel will be a positron-emitting radionuclide such as $^{19}$F which will annihilate to form two 511 keV gamma rays which will be detected by the PET camera.

In the present invention, amyloid binding compounds/probes are made which are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the thioflavin derivatives may be labeled with $^{19}$F or $^{13}$C for MRS/MRI by general organic chemistry techniques known to the art. See, e.g., March, J. ADVANCED ORGANIC CHEMISTRY: REACTIONS, MECHANISMS, AND STRUCTURE (3rd Edition, 1985), the contents of which are hereby incorporated by reference. The thioflavin derivatives also may be radiolabeled with $^{18}$F, $^{11}$C, $^{75}$Br, or $^{76}$Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The thioflavin derivatives also may be radiolabeled with $^{123}$I for SPECT by any of several techniques known to the art. See, e.g., Kulkarni, *Int. J. Rad. Appl. & Inst.* (Part B) 18: 647 (1991), the contents of which are hereby incorporated by reference. In addition, the thioflavin derivatives may be labeled with any suitable radioactive iodine isotope, such as, but not limited to $^{131}$I, $^{125}$I, or $^{123}$I, by iodination of a diazotized amino derivative directly via a diazonium iodide, see Greenbaum, F. *Am. J. Pharm.* 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio *J. Org. Chem.* 48: 4394 (1983), Goodman et al., *J. Org. Chem.* 49: 2322 (1984), and Mathis et al., *J. Labell. Comp. and Radiopharm.* 1994: 905; Chumpradit et al., *J. Med. Chem.* 34: 877 (1991); Zhuang et al., *J. Med. Chem.* 37: 1406 (1994); Chumpradit et al., *J. Med. Chem.* 37: 4245 (1994). For example, a stable triazene or tri-alkyl tin derivative of thioflavin or its analogues is reacted with a halogenating agent containing $^{131}$I, $^{125}$I, $^{123}$I, $^{76}$Br, $^{75}$Br, $^{18}$F or $^{19}$F. Thus, the stable tri-alkyl tin derivatives of thioflavin and its analogues are novel precursors useful for the synthesis of many of the radiolabeled compounds within the present invention. As such, these tri-alkyl tin derivatives are one embodiment of this invention.

The thioflavin derivatives also may be radiolabeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled thioflavin derivative can then be used to detect amyloid deposits. Preparing radiolabeled derivatives of Tc$^{99m}$ is well known in the art. See, for example, Zhuang et al., "Neutral and stereospecific Tc-99m complexes: [99mTc]N-benzyl-3,4-di-(N-2-mercaptoethyl)-amino-pyrrolidines (P-BAT)" *Nuclear Medicine & Biology* 26(2):217-24, (1999); Oya et al., "Small and neutral Tc(v)O BAT, bisaminoethanethiol (N2S2) complexes for developing new brain imaging agents" *Nuclear Medicine & Biology* 25(2):135-40, (1998); and Hom et al., "Technetium-99m-labeled receptor-specific small-molecule radiopharmaceuticals: recent developments and encouraging results" *Nuclear Medicine & Biology* 24(6):485-98, (1997).

The methods of the present invention may use isotopes detectable by nuclear magnetic resonance spectroscopy for purposes of in vivo imaging and spectroscopy. Elements particularly useful in magnetic resonance spectroscopy include $^{19}$F and $^{13}$C.

Suitable radioisotopes for purposes of this invention include beta-emitters, gamma-emitters, positron-emitters, and x-ray emitters. These radioisotopes include $^{131}$I, $^{123}$I, $^{18}$F, $^{11}$C, $^{75}$Br, and $^{76}$Br. Suitable stable isotopes for use in Magnetic Resonance Imaging (MRI) or Spectroscopy (MRS), according to this invention, include $^{19}$F and $^{13}$C. Suitable radioisotopes for in vitro quantification of amyloid in homogenates of biopsy or post-mortem tissue include $^{125}$I, $^{14}$C, and $^{3}$H. The preferred radiolabels are $^{11}$C or $^{18}$F for use in PET in vivo imaging, $^{123}$I for use in SPECT imaging, $^{19}$F for MRS/MRI, and $^{3}$H or $^{14}$C for in vitro studies. However, any conventional method for visualizing diagnostic probes can be utilized in accordance with this invention.

The method may be used to diagnose AD in mild or clinically confusing cases. This technique would also allow longitudinal studies of amyloid deposition in human populations at high risk for amyloid deposition such as Down's syndrome, familial AD, and homozygotes for the apolipoprotein E4 allele. Corder et al., *Science* 261: 921 (1993). A method that allows the temporal sequence of amyloid deposition to be followed can determine if deposition occurs long before dementia begins or if deposition is unrelated to dementia. This method can be used to monitor the effectiveness of therapies targeted at preventing amyloid deposition.

Generally, the dosage of the detectably labeled thioflavin derivative will vary depending on considerations such as age, condition, sex, and extent of disease in the patient, contraindications, if any, concomitant therapies and other variables, to be adjusted by a physician skilled in the art. Dosage can vary from 0.001 μg/kg to 10 μg/kg, preferably 0.01 μg/kg to 1.0 μg/kg.

Administration to the subject may be local or systemic and accomplished intravenously, intraarterially, intrathecally (via the spinal fluid) or the like. Administration may also be intradermal or intracavitary, depending upon the body site under examination. After a sufficient time has elapsed for the compound to bind with the amyloid, for example 30 minutes to 48 hours, the area of the subject under investigation is examined by routine imaging techniques such as MRS/MRI, SPECT, planar scintillation imaging, PET, and any emerging imaging techniques, as well. The exact protocol will necessarily vary depending upon factors specific to the patient, as noted above, and depending upon the body site under examination, method of administration and type of label used; the determination of specific procedures would be routine to the skilled artisan. For brain imaging, preferably, the amount (total or specific binding) of the bound radioactively labeled thioflavin derivative or analogue of the present invention is measured and compared (as a ratio) with the amount of labeled thioflavin derivative bound to the cerebellum of the patient. This ratio is then compared to the same ratio in age-matched normal brain.

The pharmaceutical compositions of the present invention are advantageously administered in the form of injectable compositions, but may also be formulated into well known drug delivery systems (e.g., oral, rectal, parenteral (intravenous, intramuscular, or subcutaneous), intracisternal, intravaginal, intraperitoneal, local (powders, ointments or drops), or as a buccal or nasal spray). A typical composition for such purpose comprises a pharmaceutically acceptable carrier. For instance, the composition may contain about 10 mg of human serum albumin and from about 0.5 to 500 micrograms of the labeled thioflavin derivative per milliliter of phosphate buffer containing NaCl. Other pharmaceutically acceptable carriers include aqueous solutions, non-toxic excipients, including salts, preservatives, buffers and the like, as described, for instance, in REMINGTON'S PHARMACEUTICAL SCIENCES, 15th Ed. Easton: Mack Publishing Co. pp. 1405-1412 and 1461-1487 (1975) and THE NATIONAL FORMULARY XIV., 14th Ed. Washington: American Pharmaceutical Association (1975), the contents of which are hereby incorporated by reference.

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the pharmaceutical composition are adjusted according to routine skills in the art. See, Goodman and Gilman's THE PHARMACOLOGICAL BASIS FOR THERAPEUTICS (7th Ed.).

Particularly preferred pharmaceutical compositions of the present invention are those that, in addition to specifically binding amyloid in vivo and capable of crossing the blood brain barrier, are also non-toxic at appropriate dosage levels and have a satisfactory duration of effect.

According to the present invention, a pharmaceutical composition comprising thioflavin amyloid binding compounds, is administered to subjects in whom amyloid or amyloid fibril formation are anticipated. In the preferred embodiment, such subject is a human and includes, for instance, those who are at risk of developing cerebral amyloid, including the elderly, nondemented population and patients having amyloidosis associated diseases and Type 2 diabetes mellitus. The term "preventing" is intended to include the amelioration of cell degeneration and toxicity associated with fibril formation. By "amelioration" is meant the treatment or prevention of more severe forms of cell degeneration and toxicity in patients already manifesting signs of toxicity, such as dementia.

The pharmaceutical composition comprises thioflavin amyloid binding compounds described above and a pharmaceutically acceptable carrier. In one embodiment, such pharmaceutical composition comprises serum albumin, thioflavin amyloid binding compounds and a phosphate buffer containing NaCl. Other pharmaceutically acceptable carriers include aqueous solutions, non-toxic excipients, including salts, preservatives, buffers and the like, as described, for instance, in REMINGTON'S PHARMACEUTICAL SCIENCES, 15th Ed., Easton: Mack Publishing Co., pp. 1405-1412 and 1461-1487 (1975) and THE NATIONAL FORMULARY XIV., 14th Ed. Washington: American Pharmaceutical Association (1975), and the UNITED STATES PHARMACOPEIA XVIII. 18th Ed. Washington: American Pharmaceutical Association. (1995), the contents of which are hereby incorporated by reference.

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. See, Goodman and Gilman's THE PHARMACOLOGICAL BASIS FOR THERAPEUTICS (7th Ed.).

According to the invention, the inventive pharmaceutical composition could be administered orally, in the form of a liquid or solid, or injected: intravenously or intramuscularly, in the form of a suspension or solution. By the term "pharmaceutically effective amount" is meant an amount that prevents cell degeneration and toxicity associated with fibril formation. Such amount would necessarily vary depending upon the age, weight and condition of the patient and would be adjusted by those of ordinary skill in the art according to well-known protocols. In one embodiment, a dosage would be between 0.1 and 100 mg/kg per day, or divided into smaller dosages to be administered two to four times per day. Such a regimen would be continued on a daily basis for the life of the patient. Alternatively, the pharmaceutical composition could be administered intramuscularly in doses of 0.1 to 100 mg/kg every one to six weeks.

According to the aspect of the invention which relates to a method of detecting amyloid deposits in biopsy or post-mortem tissue, the method involves incubating formalin-fixed tissue with a solution of a thioflavin amyloid binding compound chosen from structures A-E or F-J, described above. Preferably, the solution is 25-100% ethanol, (with the remainder being water) saturated with a thioflavin amyloid binding compound according to the invention. Upon incubation, the compound stains or labels the amyloid deposit in the tissue, and the stained or labeled deposit can be detected or visualized by any standard method. Such detection means include microscopic techniques such as bright-field, fluorescence, laser-confocal and cross-polarization microscopy.

The method of quantifying the amount of amyloid in biopsy or post-mortem tissue involves incubating a labeled derivative of thioflavin according to the present invention, or a water-soluble, non-toxic salt thereof, with homogenate of biopsy or post-mortem tissue. The tissue is obtained and homogenized by methods well known in the art. The preferred label is a radiolabel, although other labels such as enzymes, chemiluminescent and immunofluorescent compounds are well known to skilled artisans. The preferred radiolabel is $^{125}I$, $^{14}C$ or $^{3}H$, the preferred label substituent of an amyloid binding compound chosen from structures A-E or F-J is at least one of $R^3$-$R^{14}$. Tissue containing amyloid deposits will bind to the labeled derivatives of the thioflavin amyloid binding compounds of the present invention. The bound tissue is then separated from the unbound tissue by any mechanism known to the skilled artisan, such as filtering. The bound tissue can then be quantified through any means known to the skilled artisan. The units of tissue-bound radiolabeled thioflavin derivative are then converted to units of micrograms of amyloid per 100 mg of tissue by comparison to a standard curve generated by incubating known amounts of amyloid with the radiolabeled thioflavin derivative.

The method of distinguishing an Alzheimer's diseased brain from a normal brain involves obtaining tissue from (i) the cerebellum and (ii) another area of the same brain, other than the cerebellum, from normal subjects and from subjects suspected of having Alzheimer's disease. Such tissues are made into separate homogenates using methods well known to the skilled artisan, and then are incubated with a radiolabeled thioflavin amyloid binding compound. The amount of tissue which binds to the radiolabeled thioflavin amyloid binding compound is then calculated for each tissue type (e.g. cerebellum, non-cerebellum, normal, abnormal) and the ratio for the binding of non-cerebellum to cerebellum tissue is calculated for tissue from normal and for tissue from patients suspected of having Alzheimer's disease. These ratios are then compared. If the ratio from the brain suspected of having Alzheimer's disease is above 90% of the ratios obtained from normal brains, the diagnosis of Alzheimer's disease is made. The normal ratios can be obtained from previously obtained data, or alternatively, can be recalculated at the same time the suspected brain tissue is studied.

Molecular Modeling

Molecular modeling was done using the computer modeling program Alchemy2000 Tripost, Inc. St. Louis, Mo.) to generate the Aβ peptide chains in the anti-parallel beta-sheet conformation. Kirschner et al., *Proc. Natl. Acad. Sci. U.S.A.* 83: 503 (1986). The amyloid peptides were placed in hairpin loops (Hilbich et al., *J. Mol. Biol.* 218: 149 (1991)) and used without further structural refinement. The Aβ peptides were aligned so that alternate chains were spaced 4.76 Å apart, characteristic of beta-sheet fibrils. Kirschner, supra. Thioflavin T derivatives were energy minimized and aligned with the fibril model to maximize contact with Asp-23/Gln-15/His-13 of Aβ (1-42)

Characterization of Specific Binding to Aβ Synthetic Peptide: Affinity, Kinetics, Maximum Binding The characteristics of thioflavin derivative binding were analyzed using synthetic Aβ(1-40) and 2-(4'-[$^{11}C$]methylamino-phenyl)-benzothiazole ([N-methyl-$^{11}C$]BTA-1) in phosphate-buffered saline (pH 7.0) or glycine buffer/20% ethanol (pH 8.0) as previously described for Chysamine-G binding. Klunk et al. *Neurobiol. Aging* 15: 691 (1994).

Amino Acid Sequence for Aβ(1-40) is as follows:

| 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|
| Asp | Ala | Glu | Phe | Arg | His | Asp | Ser | Gly | Tyr | Glu | Val | His | His | Gln | Lys | Leu | Val | Phe | Phe | Ala |
| 22 | 23 | 24 | 25 | 26 | 27 | 28 | 29 | 30 | 31 | 32 | 33 | 34 | 35 | 36 | 37 | 38 | 39 | 40 | | |
| Glu | Asp | Val | Gly | Ser | Asn | Lys | Gly | Ala | Ile | Ile | Gly | Leu | Met | Val | Gly | Gly | Val | Val | | |

Preparation of Thioflavin Derivatives for Tissue Staining

Both Thioflavin S (ThS) and Thioflavin T (ThT) were utilized as pharmacophores (see, e.g., FIG. 1). It is noted that both compounds contain quaternary amines and are, therefore, quite hydrophilic as a result.

Figure 2:
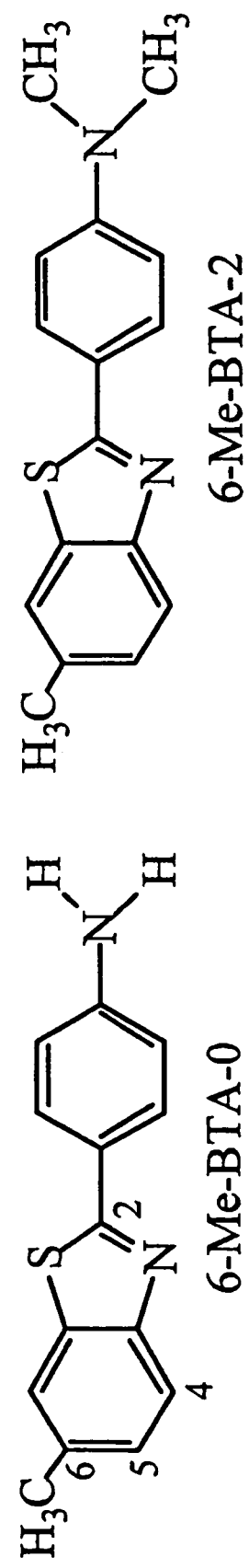
FIG. 2 Shows the structures of two thioflavin derivatives according to the invention.

[C-14]ThT was synthesized and used to determine relative lipophilicity by partitioning between octanol and phosphate-buffered saline. The log of the partition coefficient, $logP_{oct}$, was found to be 0.57 for [C-14]ThT. It was determined that the quaternary amine renders ThT too polar for use as an effective brain imaging agent. Based on the results of lipophilic Congo red derivatives (phenols uncharged at physiologic pH, but potentially ionizable with a $pK_a$ of ~8.5) (Klunk et al. WO09634853A1, WO09847969A1, WO09924394A2), the inventors removed the methyl group from the benzothiazole nitrogen for the ThT derivatives. The removal of the methyl moiety eliminated the charged quaternary amine from the heterocycle portion of the molecule, leaving an aromatic amine which typically have $pK_b$ values ~5.5. Shorthand nomenclature for the ThT derivatives is used wherein the basic backbone is designated BTA (for BenzoThiazole-Aniline). Substituents on the benzothiazole ring are placed before the 'B' and the number of methyl groups on the aniline nitrogen is placed after the 'A' (see, e.g., FIG. 2).

i. Preliminary Tissue Staining with ThT and Derivatives

Figure 3:
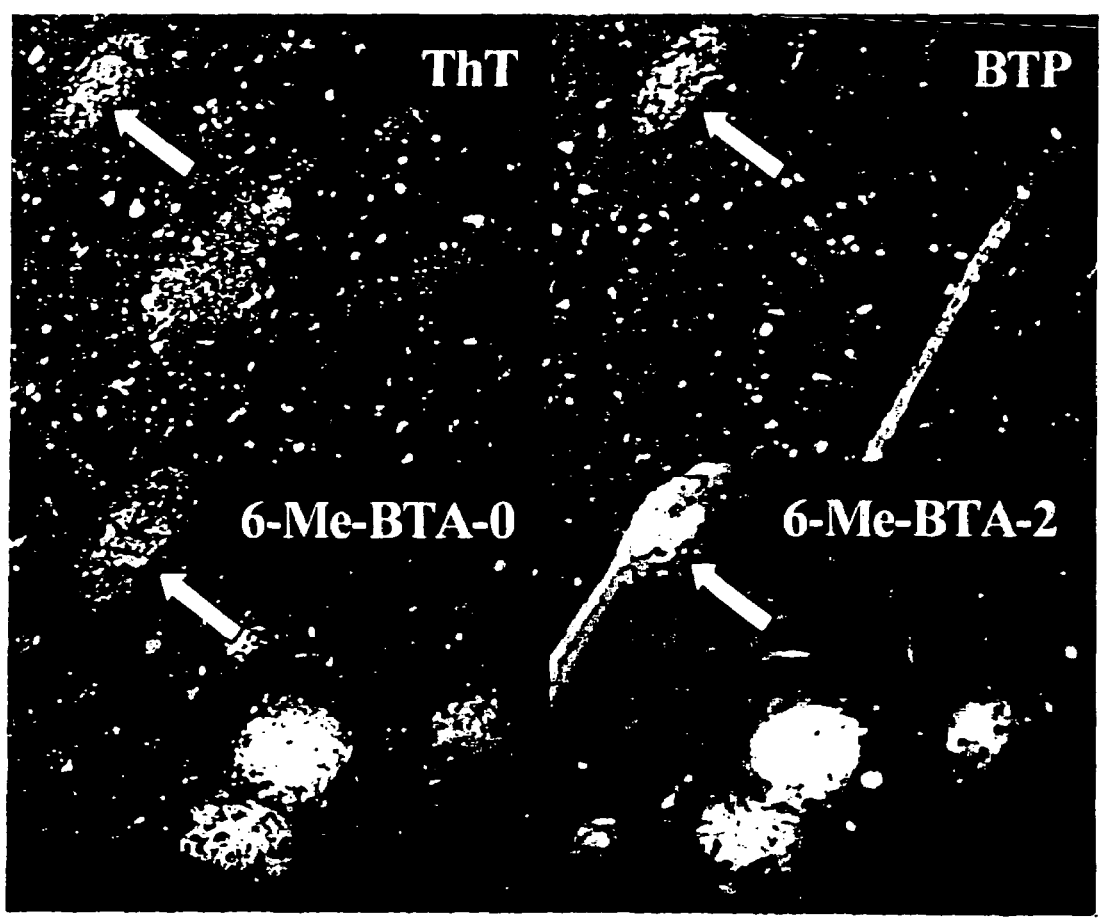
FIG. 3 Shows four serial sections of fluorescent dyed brain frontal cortex of an AD patient.

ThT (see, e.g., FIG. 1) is a fluorescent dye that has been used as a histological stain for amyloid (Burns et al., "The specificity of the staining of amyloid deposits with thioflavine T" *Journal of Pathology & Bacteriology* 94:337-344; 1967.). ThT weakly stains plaques (see, e.g., FIG. 3), tangles, neuropil threads and cerebrovascular amyloid (CVA) in AD brain. Preliminary tissue staining shows that both the primary amine 2-(4'-aminophenyl)-6-methyl-benzothiazole (6-Me-BTA-0) and the tertiary amine 2-(4'-dimethylaminophenyl)-6-methyl-benzothiazole (6-Me-BTA-2) also stain plaques and tangles in post-mortem AD brain (see, e.g., FIG. 3). Experiments in which the concentrations of 6-Me-BTA-0 and 6-Me-BTA-2 were progressively decreased showed that staining by both 6-Me-BTA-0 and 6-Me-BTA-1 could still be detected with staining solutions containing only 10 nM of the BTA compound. In contrast, BTP (2-phenylbenzothiazole) does not appear to stain plaques, however, this compound is not nearly as fluorescent as the BTA derivatives. Thus, in the development of these compounds, tissue staining has served the dual purpose of assessing specificity of staining in AD brain tissue as well as assessing binding affinity by screening staining solutions over a range of concentrations similar to that employed in the binding assays.

ii. Binding Models of Congo Red Derivatives and ThT to Aβ

There are some theories about the binding mechanism of ThT to β-amyloid, but no specific theory has been proven or accepted. However, the mechanism appears to be specific and saturable (LeVine, "Quantification of beta-sheet amyloid fibril structures with thioflavin T" *Meth. Enzymol.* 309:272-284;1999). Thus, it should be possible to localize the potential binding site(s) on Aβ and develop a binding model in a manner analogous to that used to develop the Congo red (CR)/Chrysamine-G (CG) binding model (Klunk et al., "Developments of small molecule probes for the beta-amyloid protein of Alzheimer's disease" *Neurobiol. Aging* 15:691-698;1994.) based on the following structural and binding properties. First, ThT and CG have opposite charges at physiological pH, and it is unlikely that they share a common binding site. This is supported by the lack of competition of ThT for [$^3$H]CG binding to Aβ fibrils (see, e.g., FIG. 5).

Figure 4:
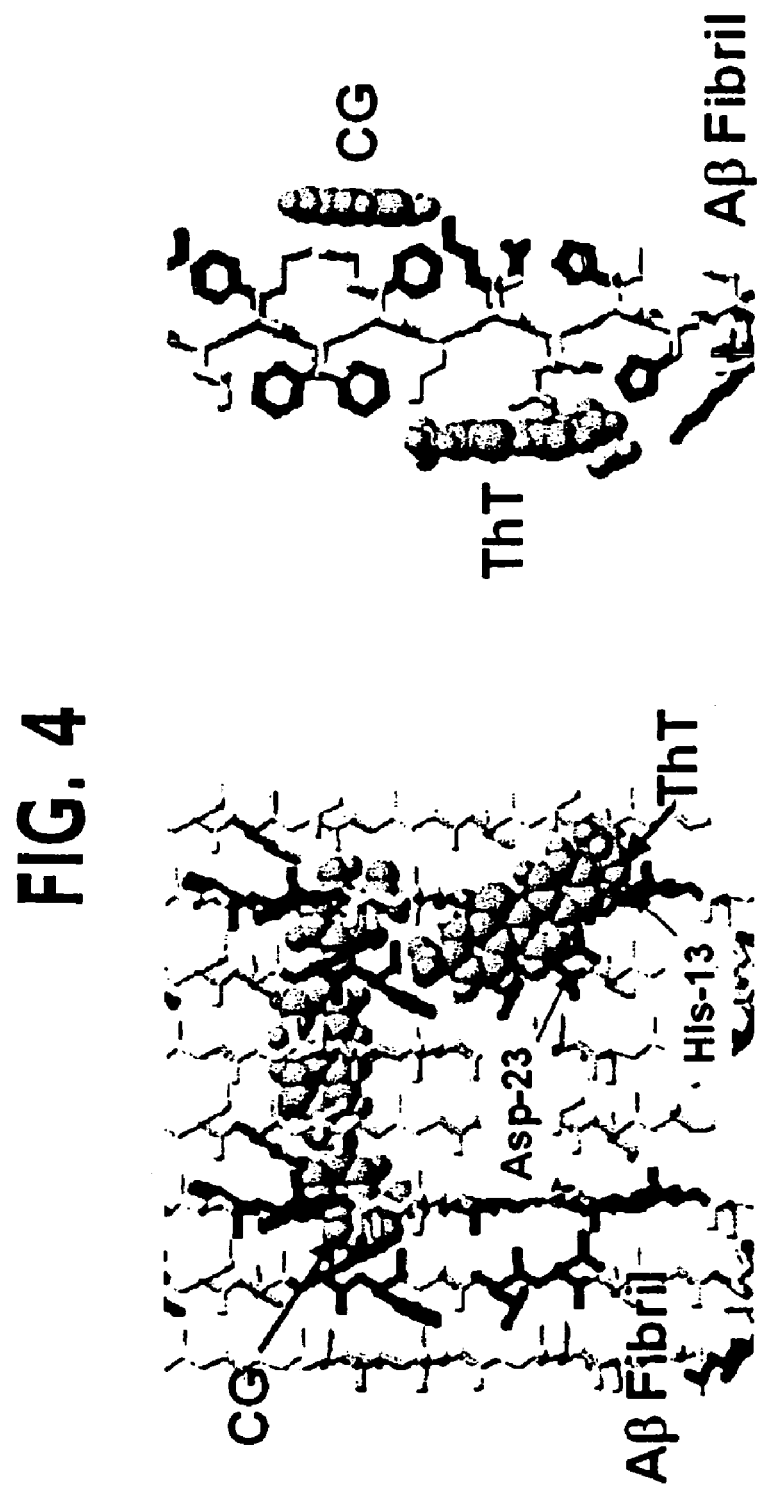
FIG. 4 Shows proposed sites of binding of Chrysamine G and Thioflavin T in β-sheet fibrils.

Previous structural studies of Aβ fibrils (Hilbich et al., "Aggregation and secondary structure of synthetic amyloid beta A4 peptides of Alzheimer's disease" *Journal of Molecular Biology* 218:149-63; 1991.) and CR and CG binding to Aβ fibrils suggested a molecular model in which CG binds through a combination of electrostatic and hydrophobic interaction to the area of Lys-16 (see, e.g., FIG. 4). The studies of LeVine (LeVine ibid) help localize the site of ThT binding to Aβ by showing that ThT binds well to Aβ12-28, but negligibly to Aβ25-35. This suggests the ThT binding site lies somewhere between residues 12 and 24 of Aβ. It is likely that the positively charged ThT (a quaternary amine) will be attracted to negatively charged (acidic) residues on Aβ. Between amino acids 12 and 24, the only acidic residues are Glu-22 and Asp-23. While both of these are candidates, the existing model predicts that Glu-22 is involved very near the Lys-16 binding site for CG. The current "working" model localizes ThT binding to the area of Asp-23—on the opposite side of the fibril from the proposed CG site. Since the key feature of ThT (and CG) binding is the presence of a beta-sheet fibril, binding must require more than just a single amino acid residue. The binding site exists when residues not normally interacting in monomers are brought together in the beta-sheet fibril. Therefore, without being bound to any one theory, it is believed that ThT also interacts via hydrogen bonds to His-13 and Gln-15 of a separate, adjacent Aβ molecule comprising the beta-sheet fibril.

iii. Radiolabeling of ThT and Radioligand Binding Assays

Assessing binding by tissue staining is useful, particularly for assessing specificity. The compound BTP, which is not very fluorescent, may not show staining either because it does not bind well enough, or because it is not fluorescent enough. In addition to the AD tissue staining, quantitative binding assays can be conducted spectrophotometrically (LeVine ibid). This assay depends on metachromatic spectral shift which occurs when ThT binds to the amyloid fibril. While this assay can be useful to individually screen highly fluorescent compounds that show this metachromatic shift, it has not been determined to be useful for competition assays. For example, it is commonly observed that test compounds (e.g., CG) quench the fluorescence of the ThT-Aβ complex (as well as ThT alone). Compounds that quench, but do not bind to the ThT site, will falsely appear to bind. Therefore, it is preferable to use radiolabeled ThT in typical radioligand binding assays with aggregated Aβ. In this assay, inhibition of radiolabeled ThT binding to Aβ trapped on filters would represent true inhibition of ThT binding and does not require the test compound to be highly fluorescent.

The following examples are given to illustrate the present invention. It should be understood, however, that the invention is not to be limited to the specific conditions or details described in these examples. Throughout the specification, any and all references to a publicly available document, including U.S. patents, are specifically incorporated into this patent application by reference.

EXAMPLES

All of the reagents used in the synthesis were purchased from Aldrich Chemical Company and used without further purification. Melting points were determined on MeI-TEMP II and were uncorrected. The $^1$H NMR spectra of all compounds were measured on Bruker 300 using TMS as internal reference and were in agreement with the assigned structures. The TLC was performed using Silica Gel 60 $F_{254}$ from EM Sciences and detected under UV lamp. Flash chromatography was performed on silica gel 60 (230-400 mesh. purchased from Mallinckrodt Company. The reverse phase TLC were purchased from Whiteman Company.

Synthesis Examples

Example 1

Synthesis of Primuline Base Derivatives

Route 1: Example of the synthesis of Primuline compounds is according to the reaction scheme shown below:

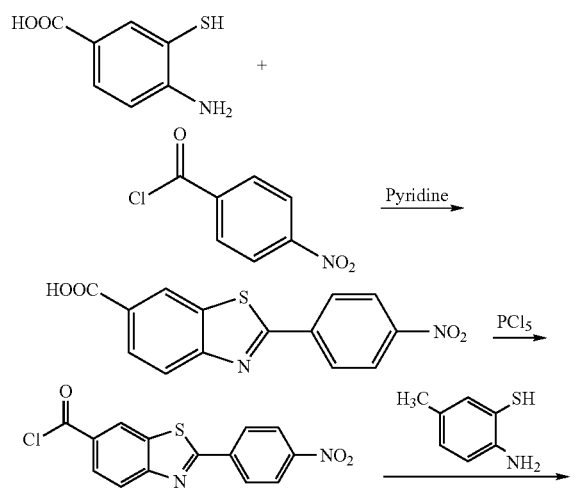

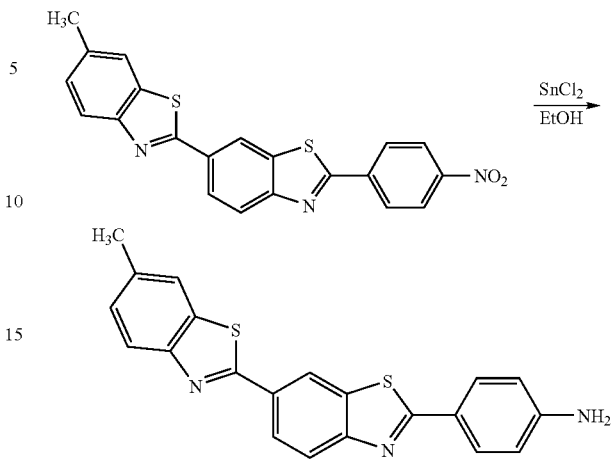

The primuline derivatives are prepared based on Schubert's method (Schubert, M. Zur Kenntnis der Dehydrothio-toluidin- and Primulin-sulfosäuren, Justus Liebigs Ann. Chem. 558, 10-33,1947) through condensation of 2-amino-5-methylthiophenol with 2-(p-nitrophenyl)-benzothiazole-6-carboxylic chloride and subsequent reduction of the nitro group with tin chloride in ethanol. Substituted derivatives of primuline base are synthesized with the appropriate substituted p-nitrobenzoylchlorides and $R^7$-$R^{10}$ substituted 2-aminothiophenol.

Following the same strategy as above, the other claimed primulin derivatives may be synthesized by substituting the appropriate substituted 3-mercapto-4-aminobenzoic acid derivative (e.g. 2-, 5-, or 6-methyl-3-mercapto-4-aminobenzoic acid), the appropriate 4-nitro-benzoyl chloride derivative (e.g. 2- or 3-methyl-4-nitro-benzoyl chloride) or the appropriate 2-amino-5-methylthiophenol derivative (e.g. 3,5-, 4,5-, or 5,6-dimethyl-2-aminothiophenol).

Example 2

Synthesis of 2-[2-(4'-aminophenyl)-ethylenyl)-benzothiazole derivatives

Route 3: Example of the synthesis of BTEA-0, 1, 2 and BTAA-0, 1, 2, which are representative of the group of BTEA and BTAA compounds was according to the reaction scheme shown below:

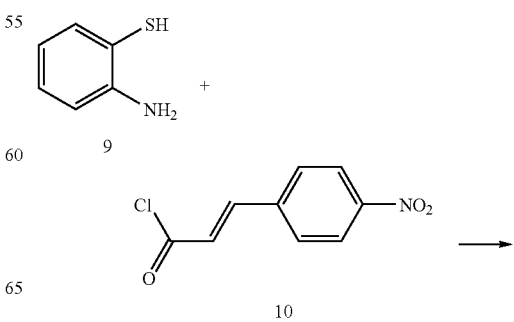

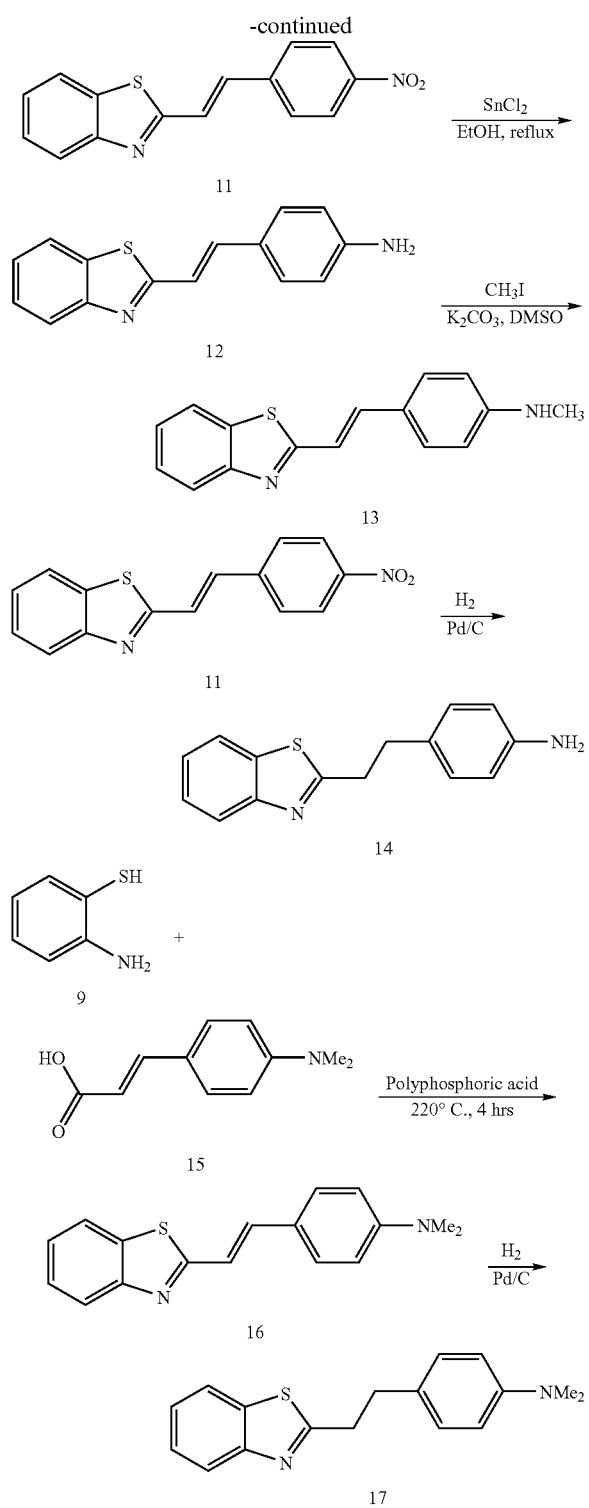

participate was collected by filtration under reduced pressure. Recrystallization from methanol gave 1.92 g (85.1%) of the product 11.

(b) 2-(4-Aminophenylethenyl)benzothiazole (12)

A mixture of 2-(4-nitrophenylethenyl)benthiazole 11 (500 mg, 1.7 mmol) and tin (II) chloride dihydrate (1.18 g, 5.2 mmol) in anhydrous ethanol (20 ml) was refluxed under $N_2$ for 4 hrs. Ethanol was removed by vacuum evaporation. The residue was dissolved into ethyl acetate (20 ml), washed with NaOH solution (1 N, 3×20 ml) and water (3×20 ml), and dried over $MgSO_4$. Evaporation to dryness gave 40 mg (8.0%) of product 12.

(c) 2-(4-Methylminophenylethenyl)benzothiazole (13)

A mixture of 2-(4-aminophenylethenyl)benzothiazole 12 (7 mg), MeI (3.9 mg) and anhydrous $K_2CO_3$(100 mg) in DMSO (anhydrous, 0.5 ml) was heated at 100° C. for 16 hrs. The reaction mixture was purified with reverse phase TLC (MeOH:$H_2O$=7:1) to give 2.5 mg (32.7%) of the product 13.

(d) 2-(4-aminophenylethylene)benzothiazole (14)

2-(4-Nitrophenylethenyl)benzothiazole (30 mg, 0.10 mmol) was dissolved in MeOH (10 mL). Pd/C(10%, 40 mg) was added and the reaction mixture was stirred under $H_2$ atmosphere at room temperature 60 hrs. The catalyst was filtrated and washed with methanol (ca. 2 ml). Evaporation of the filtrate gave the crude product which was purified with TLC (hexanes:ethyl acetate=70:40,) to give 15 mg (50%) of the product. $^1$HNMR(300 MHz, MeOH-$d_4$) δ: 7.88(d, J=8.3 Hz, 1H, H-7), 7.86(d, J=8.1 Hz, 1H, H-4), 7.48(dd, $J_1$=$J_2$=6.2 Hz, 1H, H-5 or H-6), 7.38(dd, $J_1$=$J_2$=8.2 Hz, 1H, H-5 or H-6), 6.96(d, J=6.8 Hz, 2H, H-2',6'), 6.62(d, J=6.8 Hz, 2H, H-3', 5'), 3.36(t, J=7.4 Hz, 2H, $CH_2$), 3.03(t, J=7.4 Hz, 2H, $CH_2$).

(e) 2-(4-Dimethylaminophenylethenyl)benzothiazole (16)

A mixture of 2-aminothiophenol 9 (0.51 g, 4.1 mmol) trans-4-dimethylaminocinnamic acid 14 (0.79 g, 4.1 mmol) and PPA (10 g) was heated to 220° C. for 4 hrs. The reaction mixture was cooled to room temperature and poured into 10% of potassium carbonate solution (~400 mL). The residue was collected by filtration under reduced pressure. Purification with flush column (hexanes:ethyl acetate=2:1) gave 560 mg (48.7%) of product 15 as a yellow solid.

(f) 2-(4-Dimethylaminophenylethylene)benzothiazole (17)

2-(4-Dimethylaminophenylethenyl)benzothiazole (12 mg, 0.038 mmol) was dissolved in MeOH (5 mL). Pd/C (10%, 20 mg) was added and the reaction mixture was stirred under $H_2$ atmosphere at room temperature 16 hr. The catalyst was filtrated and washed with methanol (ca. 1 ml). Evaporation of the filtrate gave 7 mg (58%) of the product. $^1$HNMR(300 MHz, Acetone-$d_6$) δ: 7.97(d, J=8.3 Hz, 1H, H-7), 7.93(d, J=8.1 Hz, 1H, H-4), 7.48(dt, J=6.2 Hz, J=1.1 Hz 1H, H-5 or H-6), 7.38(dt, J=8.2 Hz, J=1.1 Hz, 1H, H-5 or H-6), 7.13(d, J=6.8 Hz, 2H, H-2',6'), 6.68(d, J=6.8 Hz, 2H, H-3', 5'), 3.37(t, J=7.4 Hz, 2H, $CH_2$), 3.09(t, J=7.4 Hz, 2H, $CH_2$), 2.88(s, 6H, $NMe_2$).

Example 3

Synthesis of 2-(4'-aminophenyl)-benzothiazole derivatives

Route 1: Example of the synthesis of 6-MeO-BTA-0, -1, -2, which are representative of the group of BTA compounds with substituents $R_7$-$R_{10}$ as well as $R_3$-$R_6$ (Shi et al., "Antitumor Benzothiazoles. 3. Synthesis of 2-(4-Aminophenyl)

(a) Trans-2-(4-Nitrophenylethenyl)benzothiazole (11)

trans-4-Nitrocinnamyl chloride 10 (1.77 g, 9.5 mmol, 1.2 eq.) in DMF (20 ml) was added dropwise to a solution of 2-aminothiophenol 9 (1.0 g, 8.0 mmol) in DMF(15 ml) at room temperature. The reaction mixture was stirred at room temperature for overnight. The reaction mixture was poured into a solution of 10% sodium carbonate (100 ml). The benzothiazoles and Evaluation of Their Activities against Breast Cancer Cell Lines in Vitro and in Vivo" *J. Med. Chem.* 39:3375-3384, 1996):

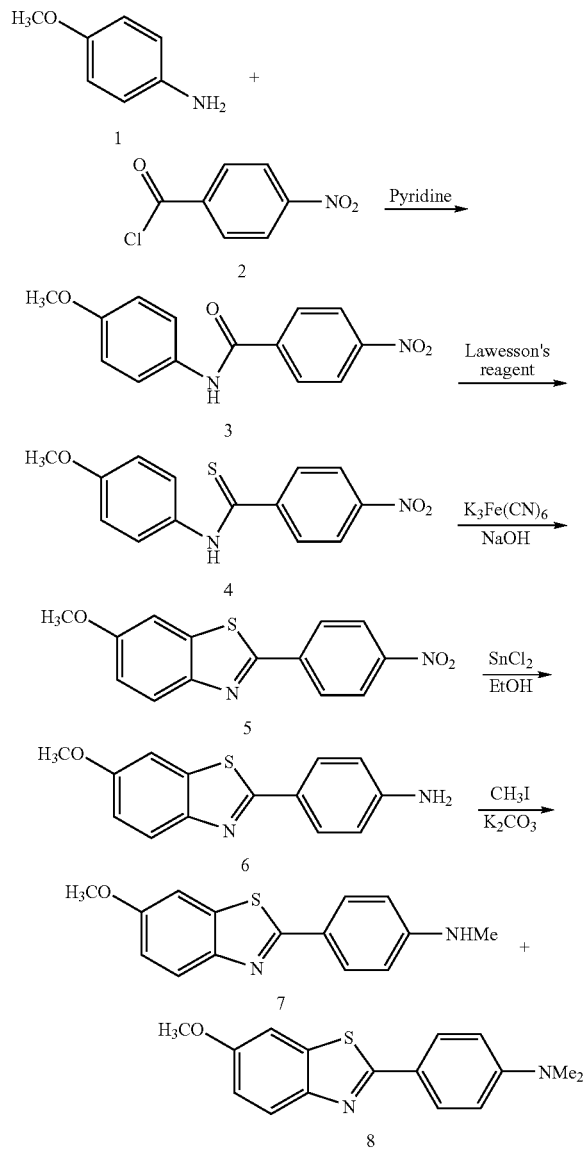

(a) 4-Methoxy-4'-nitrobenzanilide (3)

p-Anisidine 1 (1.0 g, 8.1 mmol) was dissolved in anhydrous pyridine (15 ml), 4-nitrobenzoyl chloride 2 (1.5 g, 8.1 mmol) was added. The reaction mixture was allowed to stand at room temperature for 16 hrs. The reaction mixture was poured into water and the precipitate was collected with filtrate under vacuum pressure and washed with 5% sodium bicarbonate (2×10 ml). The product 3 was used in the next step without further purification.

$^1$HNMR(300 MHz, DMSO-$d_6$) δ: 10.46(s, 1H, NH), 8.37(d, J=5.5 Hz, 2H, H-3', 5'), 8.17(d, J=6.3 Hz, 2H, H-2',6'), 7.48(d, J=6.6 Hz, 2H), 6.97(d, J=6.5 Hz, 2H), 3.75(s, 3H, MeO).

(b) 4-Methoxy-4'-nitrothiobenzanilide (4)

A mixture of 4-methoxy-4'-nitrothiobenzaniline 3 (1.0 g, 3.7 mmol) and Lawesson's reagent (0.89 g, 2.2 mmol, 0.6 equiv.) in chlorobenzene (15 mL) was heated to reflux for 4 hrs. The solvent was evaporated and the residue was purified with flush column (hexane:ethyl acetate=4:1) to give 820 mg (77.4%) of the product 4 as orange color solid. $^1$HNMR(300 MHz, DMSO-$d_6$) δ: 8.29(d, 2H, H-3',5'), 8.00(d, J=8.5 Hz, 2H, H-2',6'), 7.76(d, 2H), 7.03(d, J=8.4 Hz, 2H), 3.808.37(d, J=5.5 Hz, 2H, H-3',5'), 8.17(d, J=6.3 Hz, 2H, H-2', 6'), 7.48(d, J=6.6 Hz, 2H), 6.97(d, J=6.5 Hz, 2H), 3.75(s, 3H, MeO). (s, 3H, MeO).

(c) 6-Methoxy-2-(4-nitrophenyl)benzothiazole (5)

4-Methoxy-4'-nitrothiobenzanilides 4 (0.5 g, 1.74 mmol) was wetted with a little ethanol (~0.5 mL), and 30% aqueous sodium hydroxide solution (556 mg 13.9 mmol. 8 equiv.) was added. The mixture was diluted with water to provide a final solution/suspension of 10% aqueous sodium hydroxide. Aliquots of this mixture were added at 1 min intervals to a stirred solution of potassium ferricyanide (2.29 g, 6.9 mmol, 4 equiv.) in water (5 mL) at 80-90° C. The reaction mixture was heated for a further 0.5 h and then allowed to cool. The participate was collected by filtration under vacuum pressure and washed with water, purified with flush column (hexane:ethyl acetate=4:1) to give 130 mg (26%) of the product 5. $^1$HNMR(300 MHz, Acetone-$d_6$) δ: 8.45(m, 4H), 8.07(d, J=8.5 Hz, 1H, H-4), 7.69(s, 1H, H-7), 7.22(d, J=9.0 Hz, 1H, H-5), 3.90(s, 3H, MeO)

(d) 6-Methoxy-2-(4-aminophenyl)benzothiazole (6)

A mixture of the 6-methoxy-2-(4-nitropheyl)benzothiazbles 5 (22 mg, 0.077 mmol) and tin (II) chloride dihydrate (132 mg, 0.45 mmol) in boiling ethanol was stirred under nitrogen for 4 hrs. Ethanol was evaporated and the residue was dissolved in ethyl acetate (10 mL), washed with 1 N sodium hydroxide (2 mL) and water (5 mL), and dried over $MgSO_4$. Evaporation of the solvent gave 19 mg (97%) of the product 6 as yellow solid.

(e) 6-Methoxy-2-(4-methylaminophenyl)benzothiazole (7) and 6-Methoxy-2-(4-dimethylaminophenyl)benzothiazole (8)

A mixture of 6-methoxy-2-(4-aminophenyl)benzothiazole 6 (15 mg, 0.059 mmol), MeI (8.3 mg, 0.060 mmol) and $K_2CO_3$ (100 mg, 0.72 mmol) in DMSO (anhydrous, 0.5 ml) was heated at 100° C. for 16 hrs. The reaction mixture was purified by reverse phase TLC (MeOH:$H_2O$=7:1) to give 2.0 mg (13.3%) of 6-methoxy-2-4-methylaminophenylbenzothiazole 7 and 6 mg (40%) of 6-methoxy-2-(4-dimethylaminophenyl)benzothiazole 8. $^1$HNMR of 7 (300 MHz, Acetone-$d_6$) δ: 7.85(d, J=8.7 Hz, 2H, H-2' 6'), 7.75(dd, J=8.8 Hz, J=1.3 Hz, 1H, H-4), 7.49(d, J=2.4 Hz, 1H, H-7), 7.01(dd, J=8.8 Hz, J=2.4 Hz, H-5), 6.78(d, J=7.6 Hz, 2H, H-3' 5'), 3.84(s, 3H, MeO), 2.91(s, 3H, NMe), $^1$HNMR of 8 (300 MHz, Acetone-$d_6$)δ: 7.85(d, J=8.7 Hz, 2H, H-2' 6'), 7.75(dd, J=8.8 Hz, J=1.3 Hz, 1H, H-4), 7.49(d, J=2.4 Hz, 1H, H-7), 7.01(dd, J=8.8 Hz, J=2.4 Hz, H-5), 6.78(d, J=7.6 Hz, 2H, H-3' 5'), 3.84(s, 3H, MeO), 3.01(s, 6H, $NMe_2$), Following the same strategy as above, the other claimed 2-(4'-aminophenyl)-benzothiazole derivatives may be synthesized by substituting the appropriate substituted aniline derivative (e.g. 2-, 3-, or 4-methylaniline) and the appropriate 4-nitro-benzoyl chloride derivative (e.g. 2- or 3-methyl-4-nitro-benzoyl chloride).

Example 4

Synthesis of BTA Derivatives without $R^7$-$R^{10}$ Substitution

Route 2: Example of the synthesis of BTA-0, -1, -2 compounds, which are representative of the group of BTA compounds without R[7]-R[10] (Garmaise et al., "Anthelmintic Quaternary Salts. III. Benzothiazolium Salts" *J. Med. Chem.* 12:30-36 1969):

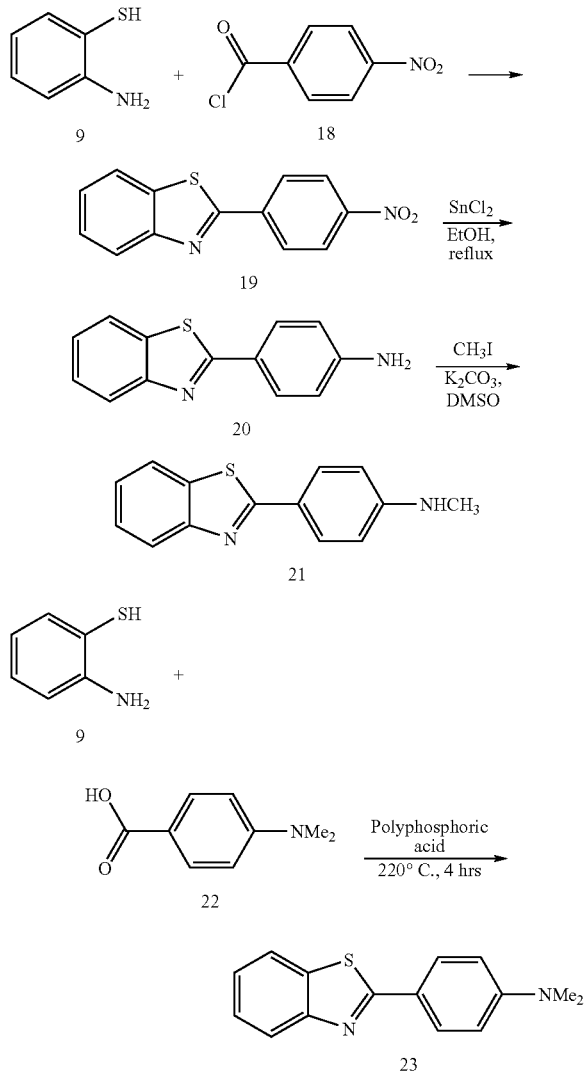

(a) 2-(4-Nitrophenyl)benzothiazole (19)

A solution of 4-nitrobenzoyl chloride (1.49 g, 8.0 mmol) in benzene anhydrous, 10 mL) was added dropwise to 2-aminothiophenol (1.0 g, 8.0 mmol in 10 ml of benzene) at room temperature. The reaction mixture was allowed to stir for 16 hr. The reaction was quenched with water (20 mL). The aqueous layer was separated and extracted with ethyl acetate (3×10 ml). The combined organic layers were dried and evaporated. The crude product was purified with flush column, (hexane:ethyl acetate=85:15) to give 1.5 g (73.2%) of product as light yellow solid.

(b) 2-(4-Aminophenyl)benzothiazole (20)

A mixture of 2-(4-nitrophenyl)benzothiazole (105 mg, 0.40 mmol) and tin (II) chloride dihydrate (205 mg, 0.91 mmol) in ethanol (20 mL) was refluxed under $N_2$ for 4 hrs. After removing ethanol by vacuum evaporation. The residue was dissolved into ethyl acetate (20 ml), and washed with NaOH solution (1 N, 3×20 ml) and water (3×20 ml), dried and evaporated to dryness to give102 mg (97%) of the product (c) 2-(4-Methylaminophenyl)benzothiazole (21) and 2-(4-dimethylaminophenyl)benzothiazole (23)

A mixture of 2-(4-aminophenyl)benzothiazole 20 (15 mg, 0.066 mmol), MeI (9.4 mg, 0.066 mg) and $K_2CO_3$(135 mg, 0.81 mmol) in DMSO (anhydrous, 0.5 ml) was heated at 100° C. for 16 hrs. The reaction mixture was purified by reverse phase TLC (MeOH:$H_2O$=6:1) to give 1.5 mg (10%) of 2-(4-methylminophenyl)benzothiazole 21 and 2.5 mg (16.7%) of 2-(4-dimethylaminophenyl)benzothiazole 23.

(d) 2-(4-Dimethylaminophenyl)benzothiazole (23)

The mixture of 2-aminothiophenol 9 (0.5 g, 4.0 mmol) 4-dimethylaminobenzoic acid 22 (0.66 g, 4.0 mmol) and PPA (10 g) was heated to 220° C. for 4 hrs. The reaction mixture was cooled to room temperature and poured into a solution of 10% potassium carbonate (~400 mL). The residue was collected by filtration under vacuum pressure to give 964 mg of the product 23, which was ca. 90% pure based on the $^1$HNMR analysis. Recrystalization of 100 mg of 23 in MeOH gave 80 mg of the pure product. $^1$HNMR (300 MHz, Acetone-$d_6$) δ: 7.12(d, J=7.7 Hz, 1H, H-7), 7.01 (d, J=9.0 Hz, 1H, H-4), 6.98(d, J=9.1 Hz, 2H, H-2',6'), 6.56(t, J=7.8 Hz, J=7.3 Hz, 1H, H-5 or H-6), 5.92(d, J=8.9 Hz, 1H, H-3',5'), 2.50(s, 6H, NMe$_2$).

Following the same strategy as above, the other claimed 2-(4'-aminophenyl)-benzothiazole derivatives may be synthesized by substituting appropriate 4-nitro-benzoyl chloride derivative (e.g. 2- or 3-methyl-4-nitro-benzoyl chloride) or appropriate 4-dimethylamino-benzoic acid derivative (e.g. 2- or 3-methyl-4-dimethylamino-benzoic acid).

Example 5

Synthesis of bis-2,2'-(4'-aminophenyl)-dibenzothiazole derivatives

Route 1: Following the general procedure for 6-MeO-BTA compounds described above but substituting benzidine for p-anisidine and using 16 equivalents of 4-nitrobenzoyl chloride results in the following compound:

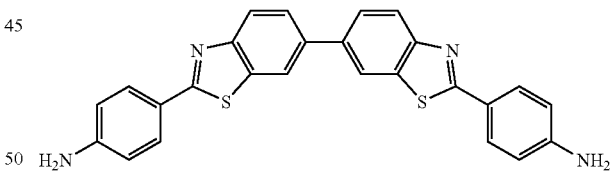

Following the same strategy as above, the other bis-2,2'-(4'-aminophenyl)-dibenzothiazole derivatives may be synthesized via the appropriate substituted benzidine dervative (e.g. 2,2'-, 3,3'-dimethylbenzidine) and the appropriate 4-nitro-benzoyl chloride derivative (e.g. 2- or 3-methyl-4-nitro-benzoyl chloride).

Route 2: The unsymmetric bis-2,2'-(4'-aminophenyl)-dibenzothiazole derivatives are synthesized through palladium catalyzed Suzuki coupling of the appropriate substituted 6-iodo-(2-p-nitrophenyl)benzothiazoles, which can be prepared following the same strategy as 6-MeO-BTA compounds and subsequent reduction of nitro groups (Ishiyama et al., "Palladium (O)-Catalyzed Cross-Coupling Reaction of Alkoxydiboron with Haloarenes: A Direct Procedure for Arylboronic Esters" *Tetrahedron Lett.*, 38, 3447, 1997).

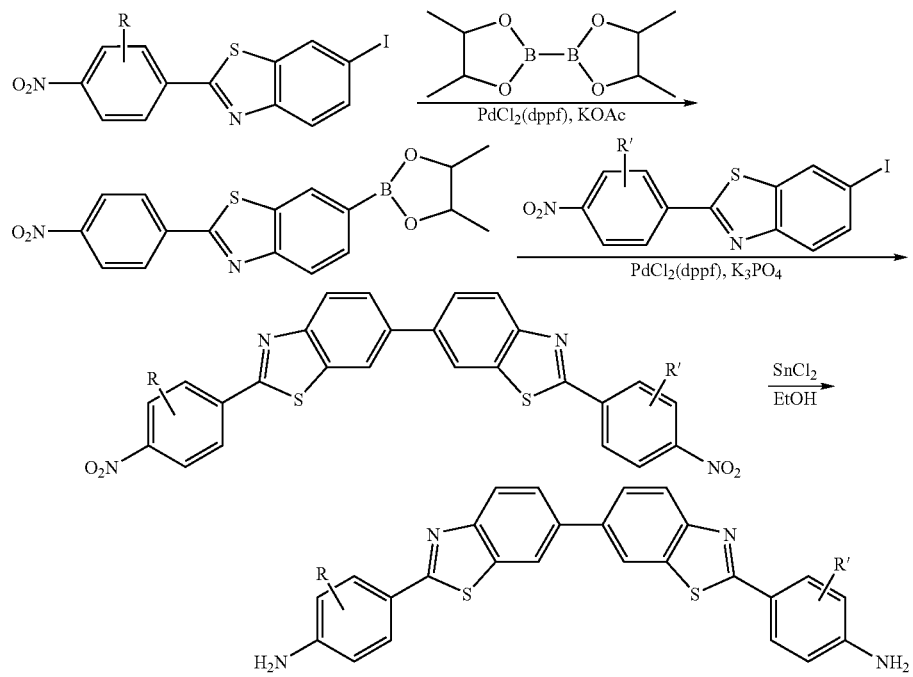

Biological Examples

Example 6

Figure 5:
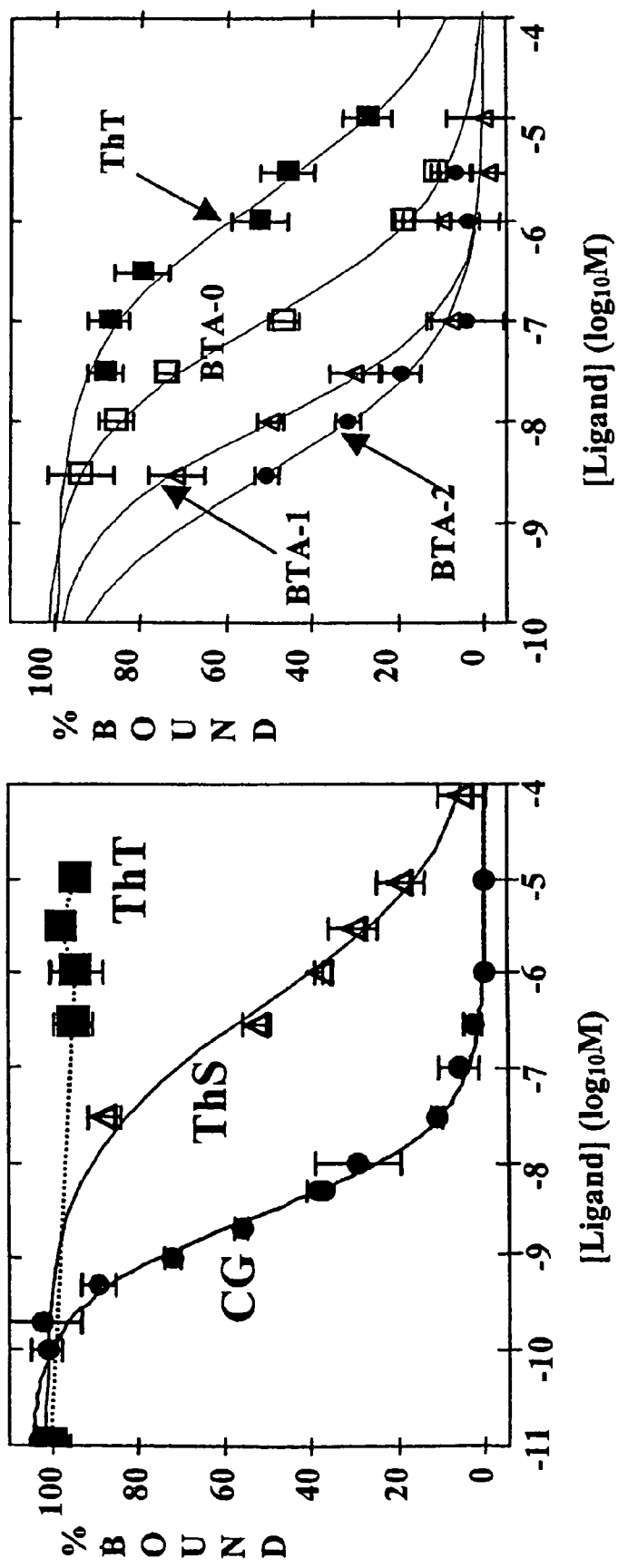
FIG. 5 Shows competition assay using Chrysamine G, Thioflavin S and Thioflavin T, and derivatives of the present invention (BTA-0, BTA-1 and BTA-2)

Determination of Affinity for Aβ and Brain Uptake of Thioflavin Derivatives Initial competitive binding studies using [³H]CG and synthetic Aβ(1-40) were conducted to determine if CG, ThS and ThT bound to the same site(s). It has been determined that ThS competed with [³H]CG for binding sites on Aβ (1-40), but ThT did not (see, e.g., FIG. 5). High specific activity [N-methyl-¹¹C]BTA-1 (see Table 1) was then synthesized by methylation of BTA-0. Bindings studies were performed with [N-methyl-¹¹C]BTA-1 and 200 nM Aβ(1-40) fibrils. The specific binding of [N-methyl-¹¹C]BTA-1 was ~70%. FIG. 5 (see the right panel) shows competition curves for Aβ sites by ThT, BTA-0, BTA-1, and BTA-2 using the [N-methyl-¹¹C]BTA-1 binding assay. The Ki's were: 3.0±0.8 nM for BTA-2; 9.6±1.8 nM for BTA-1; 100±16 nM for BTA-0; and 1900±510 nM for ThT. Not only is the quaternary amine of ThT not necessary for binding to Aβ fibrils, it appears to decrease binding affinity as well.

In Table 1 below are five different ¹¹C-labeled BTA derivatives where their in vitro binding properties, logP values, and in vivo brain uptake and retention properties in mice have been determined.

TABLE 1

In vitro and in vivo properties of several promising ¹¹C-labeled Thioflavin T derivatives.

| Structure of ¹¹C-Labeled BTA Compound | $K_i$ (nM) to Aβ fibrils | logP | Mouse Brain Uptake @ 2 min (% ID/g*kg) | Mouse Brain Uptake @ 30 min (% ID/g*kg) | Ratio of 2 min/30 min Uptake Values |
|---|---|---|---|---|---|
| [N-methyl-¹¹C]6-Me-BTA-1 | 21 | 3.3 (est.) | 0.32 ± 0.07 | 0.17 ± 0.05 | 1.9 |
| [N-methyl-¹¹C]6-Me-BTA-2 | not tested | 3.9 (est.) | 0.15 ± 0.06 | 0.16 ± 0.02 | 0.9 |

TABLE 1-continued

In vitro and in vivo properties of several promising ¹¹C-labeled Thioflavin T derivatives.

| Structure of ¹¹C-Labeled BTA Compound | $K_i$ (nM) to Aβ fibrils | logP | Mouse Brain Uptake @ 2 min (% ID/g*kg) | Mouse Brain Uptake @ 30 min (% ID/g*kg) | Ratio of 2 min/30 min Uptake Values |
|---|---|---|---|---|---|
| 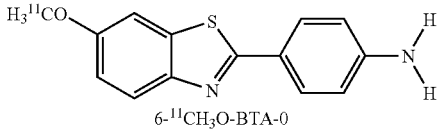 6-¹¹CH₃O-BTA-0 | 30 | 1.9 (est.) | 0.60 ± 0.04 | 0.39 ± 0.05 | 1.5 |
| 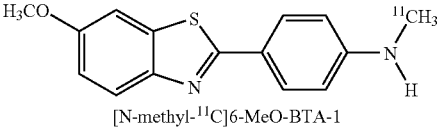 [N-methyl-¹¹C]6-MeO-BTA-1 | 5.7 | 2.7 | 0.43 ± 0.11 | 0.094 ± 0.038 | 4.6 |
|  [N-methyl-¹¹C]6-MeO-BTA-2 | 2.3 | 3.3 (est.) | 0.32 ± 0.09 | 0.42 ± 0.10 | 0.8 |
| 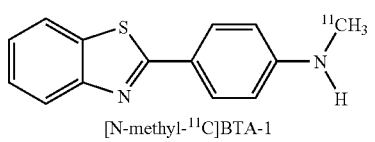 [N-methyl-¹¹C]BTA-1 | 9.6 | 2.7 | 0.44 ± 0.14 | 0.057 ± 0.010 | 7.7 |

The data shown in Table 1 are remarkable, particularly for the ¹¹C-labeled 6-MeO-BTA-1 and BTA-1 derivatives. These compounds displayed relatively high affinity for Aβ, with Ki values <10 nM, and readily entered mouse brain with uptake values >0.4% ID/g*kg (or >13% ID/g for 30 g animals). Moreover, the 30 min brain radioactivity concentration values were less than 0.1% ID/g*kg, resulting in 2 min-to-30 min concentration ratios >4. Both of the N,N-dimethyl compounds cleared less rapidly from mouse brain tissue than the N-methyl derivatives. Likewise, the only primary amine currently testable, 6-MeO-BTA-0, showed poor brain clearance. This surprising and unexpected result supports the specific use of the secondary amine (e.g. —NHCH₃) as in vivo imaging agent.

Example 7

In Vivo PET Imaging Experiments in Baboons

Figure 6:
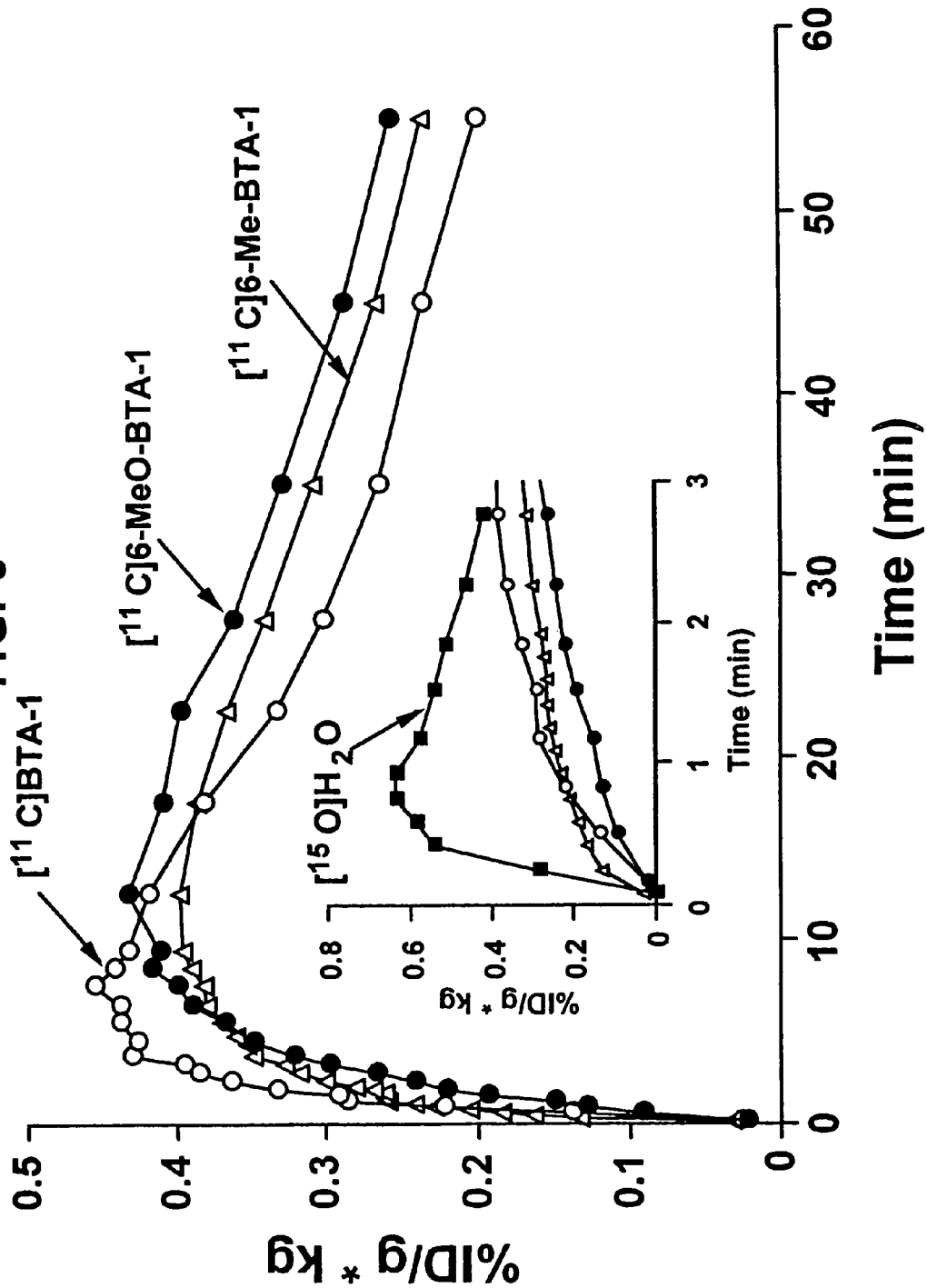
FIG. 6 Shows time course radioactivity in the frontal cortex of baboons injected with labeled BTA-1; 6-Meo-BTA-1 and 6-Me-BTA-1.

Large amounts of high specific activity (>2000 Ci/mmol) ¹¹C-labeled BTA-1, 6-Me-BTA-1, and 6-MeO-BTA-1 were prepared for brain imaging studies in 20-30 kg anesthetized baboons using the Siemens/CTI HR+ tomograph in 3D data collection mode (nominal FWHM resolution 4.5 mm). Brain imaging studies were conducted following the intravenous injection of 3-5 mCi of radiotracer. Typical attenuation- and decay-corrected time-activity curves for a frontal cortex region of interest for each of the three compounds are shown in FIG. 6. It is noted that the absolute brain uptake of these 3 compounds in baboons is very similar to that in mice (i.e., about 0.47 to 0.39% ID/g*kg). However, the normal brain clearance rate of all three radiotracers is considerably slower in baboons compared to mice, with peak-to-60 min ratios in the range of 2.4 to 1.6 compared to ratios as high as 7.7 at 30 min in mice. The rank order of maximum brain uptake and clearance rate of the three compounds were also the same in mice and baboons. Brain uptake of the radiotracers did not appear to be blood flow-limited (FIG. 6, inset). Arterial blood samples in the baboons following the injection of all three compounds were obtained, and showed that their metabolic profiles were quite similar. Only highly polar metabolites that eluted near the void volume (4 mL) of the reverse-phase analytical HPLC column were observed in the plasma at all time points following injection, while the unmetabolized tracer eluted at about 20 mL. Typical amounts of unmetabolized injectate in plasma for all three compounds were about: 90% at 2 min; 35% at 30 min; and 20% at 60 min.

Figure 7:
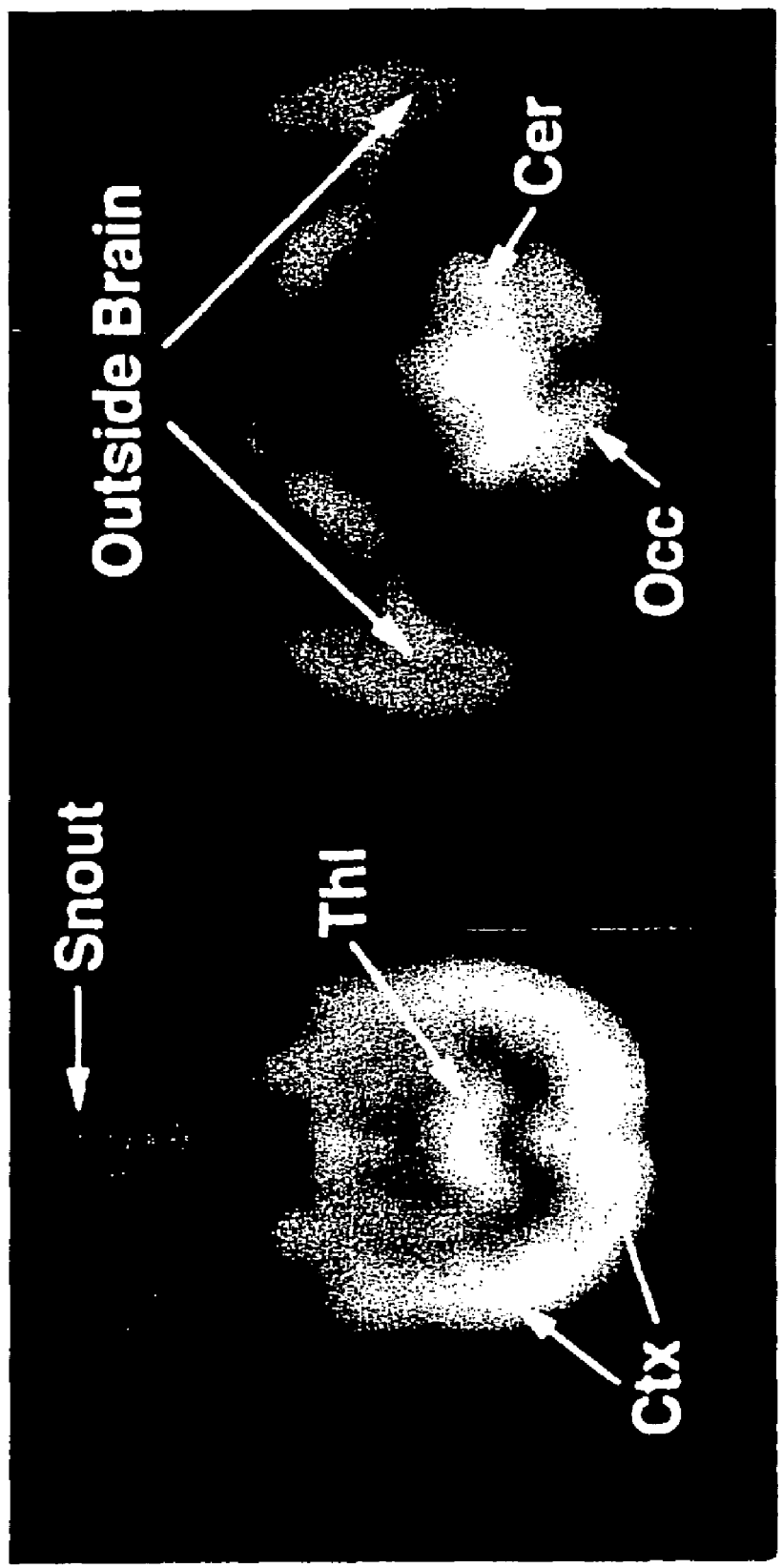
FIG. 7 Shows a tranverse positron emission tomography image of two levels of baboon brain following i.v. injection of [N-methyl-$^{11}$C]BTA-1.

Transverse PET images at two levels of baboon brain following the i.v. injection of 3 mCi of [N-methyl-¹¹C] BTA-1 are shown in FIG. 7. The emission files collected 5-15 min post injection were summed to provide the images. Brain regions include: Ctx (cortex); Thl (thalamus); Occ (occipital cortex); and Cer (cerebellum). Note the uniform distribution of radioactivity throughout the brain, indicating lack of regional binding specificity in normal brain.

Example 8

Staining Amyloid Deposits in Post-mortem AD and Tg Mouse Brain

Postmortem brain tissue sections from AD brain and an 8 month old transgenic PS1/APP [explain what this model is used to show] mouse were stained with unlabeled BTA-1. The PS1/APP mouse model combines two human gene mutations known to cause Alzheimer's disease in a doubly transgenic mouse which deposits Aβ fibrils in amyloid plaques in the brain beginning as early as 3 months of age.

Figure 8:
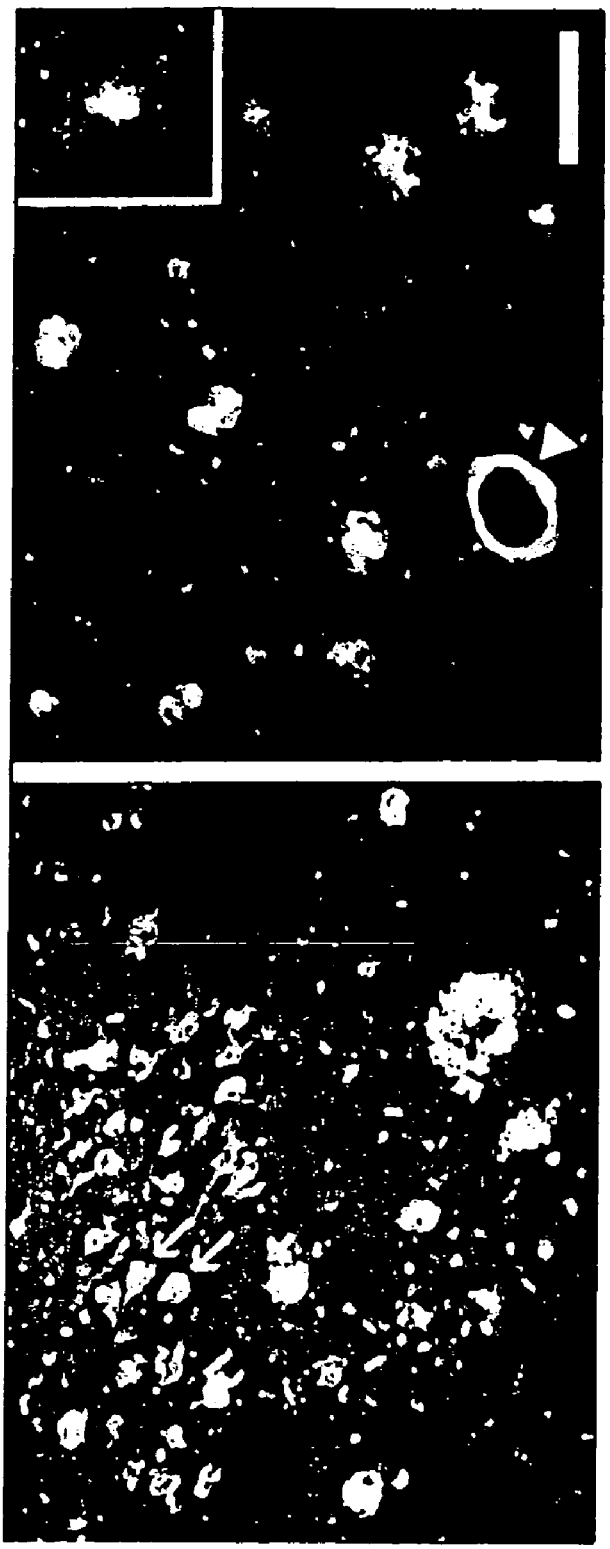
FIG. 8 Shows post-mortem sections of human and transgenic mouse brain stained with a derivative of the present invention (BTA-1).

Typical fluorescence micrographs are shown in FIG. 8, and the staining of amyloid plaques by BTA-1 in both postmortem AD and PS1/APP brain tissue is clearly visible. Cerebrovascular amyloid also was brightly stained (FIG. 8, right). The other characteristic neuropathological hallmark of AD brain, neurofibrillary tangles (NFT), are more faintly stained by BTA-1 in AD brain (FIG. 8, left). NFT have not been observed in transgenic mouse models of amyloid deposition.

Example 9

In Vivo Labeling and Detection of Amyloid Deposits in Transgenic Mice

Figure 9:
FIG. 9 Shows in vivo labeling of amyloid plaques and vascular amyloid stained by a derivative of the present invention (BTA-1) in living transgenic mice imaged with multiphoton microscopy.

Three 17 month-old PS1/APP transgenic mice were injected intraperitoneally (ip) with a single dose of 10 mg/kg of BTA-1 in a solution of DMSO, propylene glycol, and pH 7.5 PBS (v/v/v 10/45/45). Twenty-four hours later, multiphoton fluorescence microscopy was employed to obtain high resolution images in the brains of living mice using a cranial window technique. Typical in vivo images of BTA-1 in a living PS1/APP mouse are shown in FIG. 9, and plaques and cerebrovascular amyloid are clearly distinguishable. The multiphoton microscopy studies demonstrate the in vivo specificity of BTA-1 for Aβ in living PS1/APP transgenic mice.

Other embodiments of the invention will be apparent to those skilled in the art from consideration of the specification and practice of the invention disclosed herein. It is intended that the specification be considered as exemplary only, with the true scope and spirit of the invention being indicated by the following claims.

As used herein and in the following claims, singular articles such as "a", "an", and "one" are intended to refer to singular or plural.

What is claimed is:

1. An amyloid binding compound of the following formula or a water soluble, non-toxic salt thereof:

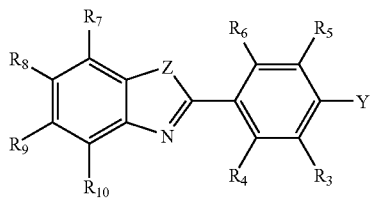

wherein
Z is S, NR', O or CR',
wherein when Z is CR', then the correct tautomeric form of the heterocyclic ring containing Z and N is an indole in which R' is H or a lower alkyl group:

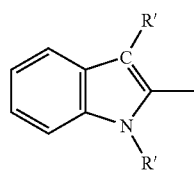

Y is $NR^1R^2$, $OR^2$, or $SR^2$;

wherein the nitrogen of

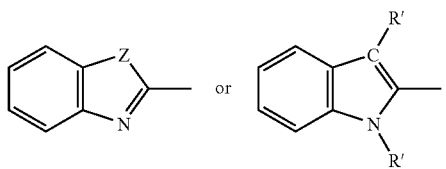

is not a quaternary amine;

each $R^1$ and $R^2$ independently is selected from the group consisting of H, a lower alkyl group, $(CH_2)_nOR'$ (wherein n=1, 2, or 3), $CF_3$, $CH_2—CH_2X$, $CH_2—CH_2—CH_2X$ (wherein X=F, Cl, Br or I), (C=O)—R', $R_{ph}$, and $(CH_2)_nR_{ph}$ (wherein n=1, 2, 3, or 4 and $R_{ph}$ represents an unsubstituted or substituted phenyl group, wherein substituents of $R_{ph}$ are selected from the group consisting of F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, (C=O)N(R')$_2$, O(CO)R', OR', SR', COOR' (wherein R' is H or a lower alkyl group), a tri-alkyl tin and a chelating group (with or without a chelated metal group) of the form W-L or V-W-L, wherein V is selected from the group consisting of —COO—, —CO—, —$CH_2O$— and —$CH_2NH$—; W is —$(CH_2)$, where n=0,1,2,3,4, or 5; and L is:

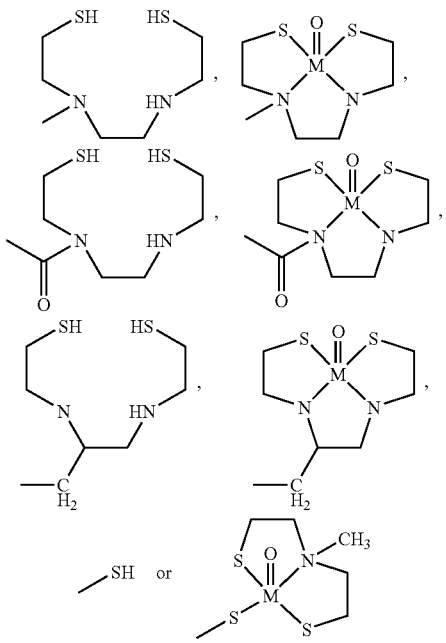

wherein M is selected from the group consisting of Tc and Re;
and R' is H or a lower alkyl group);
each $R^3$-$R^{10}$ independently is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, (C=O)N(R')$_2$, O(CO)R', OR', SR', COOR', $R_{ph}$, CR'=CR'—$R_{ph}$, $CR_2'$—$CR_2'$-

$R_{ph}$ (wherein $R_{ph}$ represents an unsubstituted or substituted phenyl group wherein R' is H or a lower alkyl group), a tri-alkyl tin and a chelating group (with or without a chelated metal group) of the form W-L or V-W-L, wherein V is selected from the group consisting of —COO—, —CO—, —CH$_2$O— and —CH$_2$NH—; W is —(CH$_2$)$_n$ where n=0,1,2,3,4, or 5; and L is:

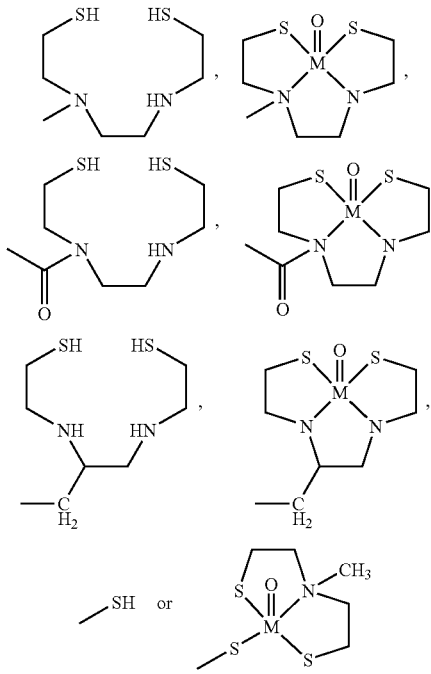

wherein M is selected from the group consisting of Tc and Re;

or each $R^1$ and $R^2$ is a chelating group (with or without a chelated metal group) of the form W-L, wherein W is —(CH$_2$)$_n$ where n=2,3,4, or 5; and L is:

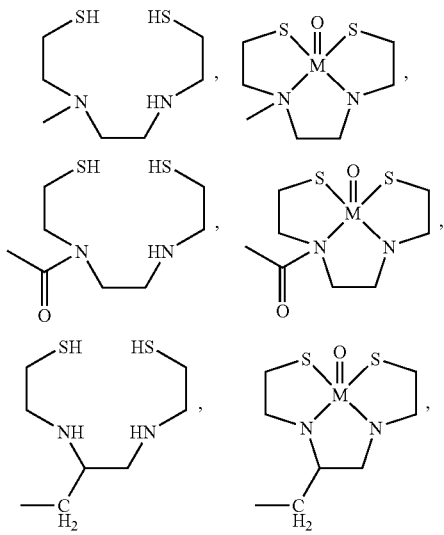

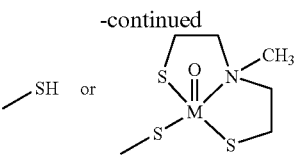

wherein M is selected from the group consisting of Tc and Re;

or wherein each $R^3$-$R^{10}$ independently is selected from the group consisting of a chelating group (with or without a chelated metal ion) of the form W-L and V-W-L, wherein V is selected from the group consisting of —COO—, and —CO—; W is —(CH$_2$)$_n$ where n=0,1, 2,3,4, or 5; L is:

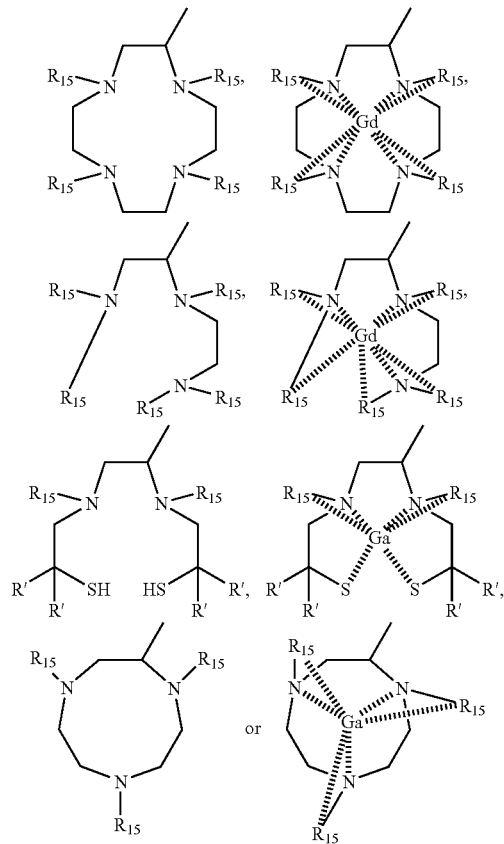

and wherein $R^{15}$ independently is selected from the following:

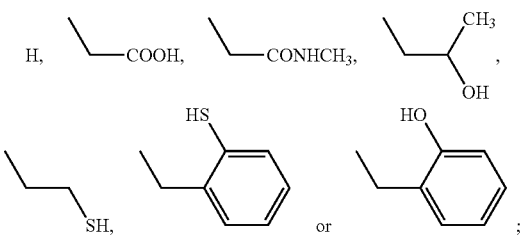

or an amyloid binding, chelating compound (with or without a chelated metal group) or a water soluble, non-toxic salt thereof of the form:

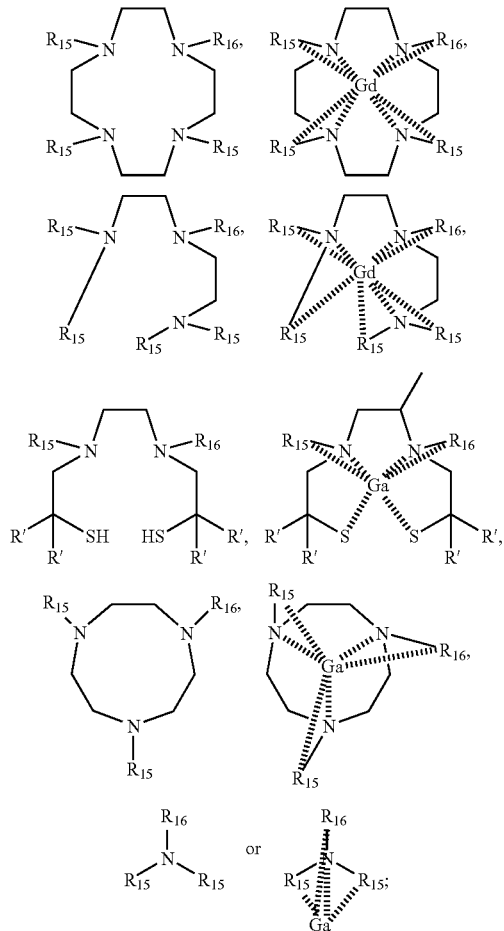

wherein $R^{15}$ independently is selected from the following:

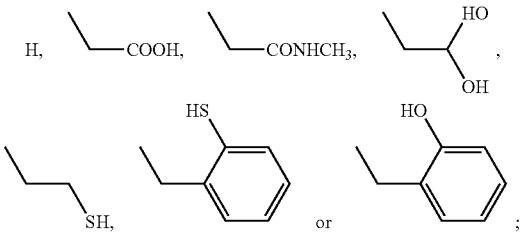

and $R^{16}$ is

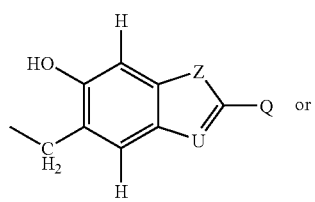

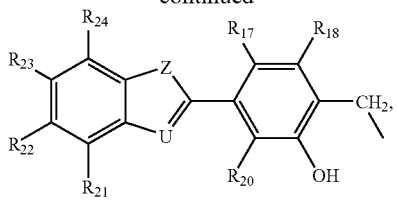

wherein Q is independently selected from one of the following structures:

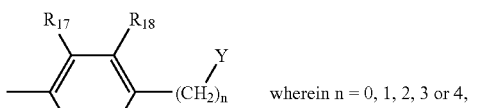

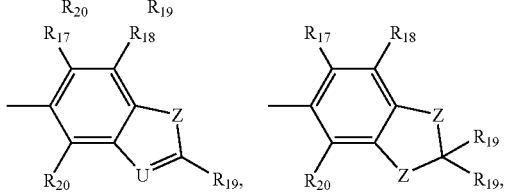

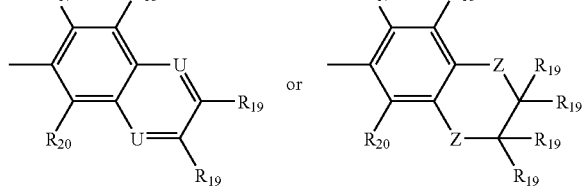

Z is S, NR', O, or C(R')$_2$ in which R' is H or a lower alkyl group;

U is N or CR';

Y is NR$^1$R$^2$, OR$^2$, or SR$^2$;

each $R^{17}$-$R^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group and wherein R' is H or a lower alkyl group);

wherein at least one of the substituents $R^1$-$R^{10}$ is selected from the group consisting of $^3$H, $^{131}$I, $^{125}$I, $^{123}$I, $^{76}$Br, $^{75}$Br, $^{18}$F, CH$_2$—CH$_2$—X*, O—CH$_2$—CH$_2$—X*, CH$_2$—CH$_2$—CH$_2$—X*, O—CH$_2$—CH$_2$—CH$_2$—X* (wherein X*=$^{131}$I, $^{123}$I, $^{76}$Br, $^{75}$Br or $^{18}$F), $^{19}$F, $^{125}$I, a carbon-containing substituent selected from the group consisting of lower alkyl, (CH$_2$)$_n$OR', CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', (C=O)N(R')$_2$, O(CO)R', COOR', CR'=CR'—R$_{ph}$ and CR$_2$'—CR$_2$'—R$_{ph}$ wherein at least one carbon is $^{11}$C, $^{13}$C or $^{14}$C and a chelating group (with chelated metal group) of the form W-L* or V-W-L*, wherein V is selected from the group consisting of —COO—, —CO—, —CH$_2$O— and —CH$_2$NH—; W is —(CH$_2$), where n=0,1,2,3,4, or 5; and L* is:
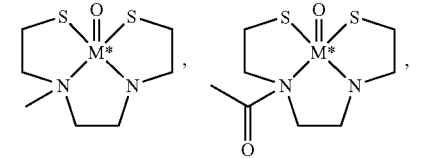
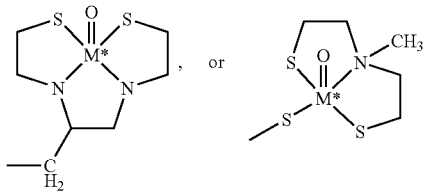
wherein M* is $^{99m}$Tc;
or L* is:
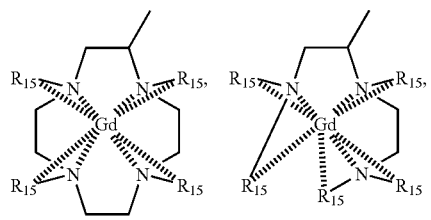
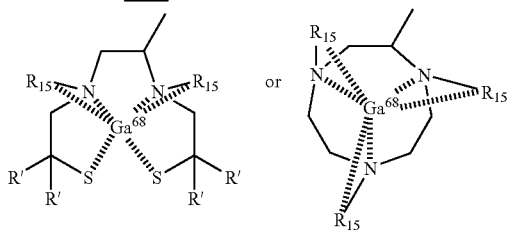
and wherein R$^{15}$ independently is selected from the following:
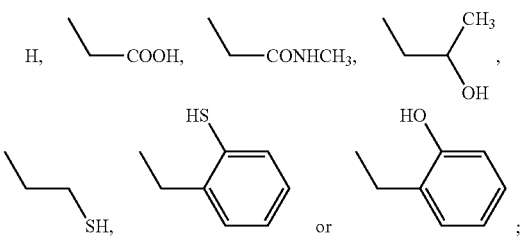
or a chelating compound (with chelated metal group) of the form:
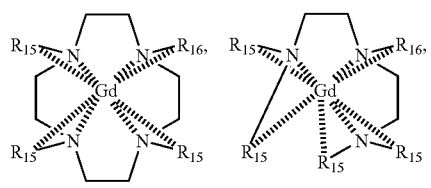
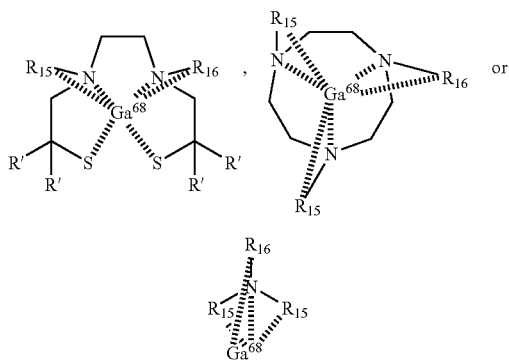
wherein R$^{15}$ independently is selected from the following:
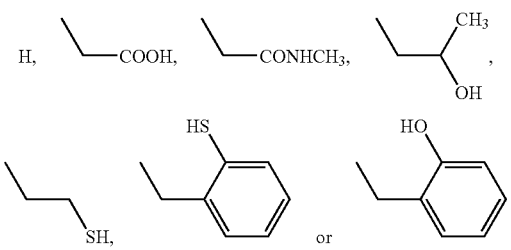
and R$^{16}$ is
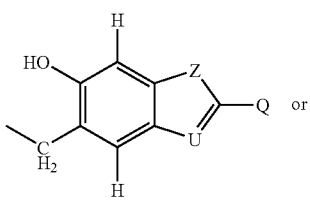
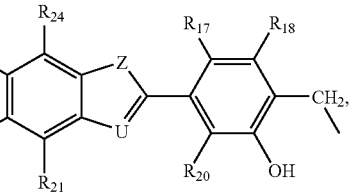
wherein Q is independently selected one of the following structures:
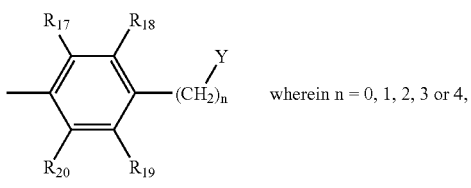 wherein n = 0, 1, 2, 3 or 4, -continued

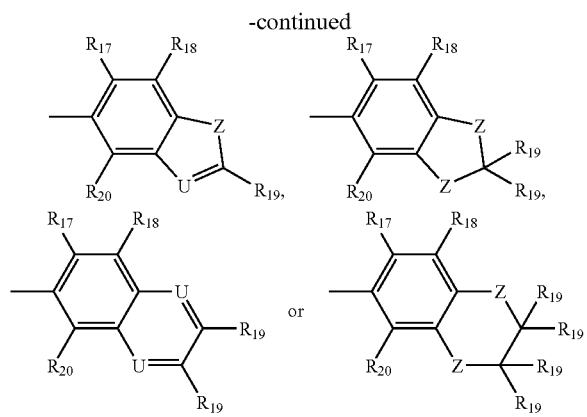

Z is S, NR', O, or C(R')$_2$ in which R' is H or a lower alkyl group;
U is N or CR';
Y is NR$^1$R$^2$, OR$^2$, or SR$^2$;
wherein each R$^{17}$—R$^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group and wherein R' is H or a lower alkyl group).

2. The compound of claim 1, wherein the radiolabel of one of substituents R$^3$-R$^{10}$ is selected from the group consisting of $^{131}$I, $^{123}$I, $^{18}$F, $^{11}$C, $^{75}$Br and $^{76}$Br.

3. The compound of claim 2, wherein the radiolabel of one of substituents R$^3$-R$^{10}$ is selected from the group consisting of $^{11}$C and $^{18}$F.

4. The compound of claim 1, wherein Z=S, Y=N, R$^1$=H; and R$^2$ is selected from the group consisting of (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and (CH$_2$)$_n$R$_{ph}$ (wherein n=1, 2, 3, or 4) wherein when R$^2$ is CH$_2$R$_{ph}$ R$^8$ is not CH$_3$.

5. The compound of claim 1, wherein Z=S, Y=N, R$^1$=H, R'=H, R$^2$=CH$_3$ and R$^3$-R$^{10}$ are H.

6. The compound of claim 1, wherein Z=S, Y=O, R'=H, R$^2$=CH$_3$ and R$^3$-R$^{10}$ are H.

7. The compound of claim 1, wherein Z=S, Y=N, R'=H, R$^1$-R$^4$=H, R$^5$=I, and R$^6$-R$^{10}$ are H.

8. The compound of claim 1, wherein Z=S, Y=N, R'=H, R$^1$-R$^4$=H, R$^5$=I, R$^8$OH and R$^6$-R$^7$ and R$^9$-R$^{10}$ are H.

9. The compound of claim 1, wherein, Z=S, Y=N, R$^1$=H, R'=H, R$^2$=CH$_2$—CH$_2$—CH$_2$—F and R$^3$-R$^{10}$ are H.

10. The compound of claim 1, wherein, Z=S, Y=O, R'=H, R$^2$=CH$_2$—CH$_2$—F and R$^3$-R$^{10}$ are H.

11. The compound of claim 1, wherein Z=S, Y=N, R'=H, R$^1$-R$^7$=H, R$^8$=O—CH$_2$—CH$_2$—F and R$^9$-R$^{10}$ are H.

12. The compound of claim 1, wherein Z=S, Y=N, R'=H, R$^1$=CH$_3$, R$^2$-R$^7$=H, R$^8$=O—CH$_2$—CH$_2$—F and R$^9$-R$^{10}$ are H.

13. The compound of claim 4, wherein at least one of the substituents R$^3$-R$^{10}$ is selected from the group consisting of CN, OCH$_3$, OH and NH$_2$.

14. The compound of claim 1, wherein R$^1$=H, R$^2$=CH$_3$ and R$^8$ is selected from the group consisting of CN, CH$_3$, OH, OCH$_3$ and NH$_2$.

15. The compound of claim 14, wherein R$^3$-R$^7$ and R$^9$-R$^{10}$ are H.

16. The compound of claim 1, having the structure:

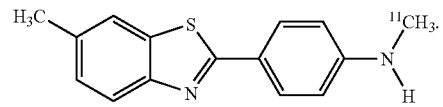

17. The compound of claim 1, having the structure:

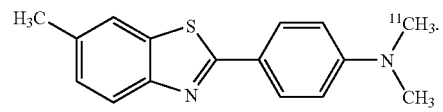

18. The compound of claim 1, having the structure:

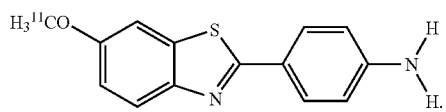

19. The compound of claim 1, having the structure:

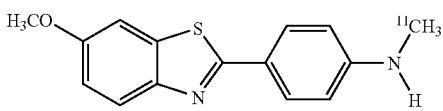

20. The compound of claim 1, having the structure:

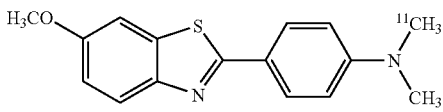

21. The compound of claim 1, having the structure:

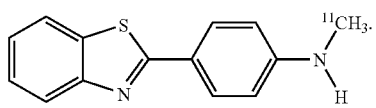

22. A method for synthesizing a compound of claim 1 having at least one of the substituents R$^3$-R$^{10}$ selected from the group consisting of $^{131}$I, $^{125}$I, $^{123}$I, $^{76}$Br, $^{75}$Br, $^{18}$F, and $^{19}$F, comprising the step of labeling a compound of claim 1, wherein Z=S, Y=N, R$^1$=H and at least one of the substituents R$^3$-R$^{10}$ is a tri-alkyl tin, by reaction of the compound with a $^{131}$I, $^{125}$I, $^{123}$I, $^{76}$Br, $^{75}$Br, $^{18}$F, or $^{19}$F containing substance.

23. A pharmaceutical composition for in vivo imaging of amyloid deposits, comprising (a) a compound of claim 1 and (b) a pharmaceutically acceptable carrier.

24. A pharmaceutical composition for in vivo imaging of amyloid deposits, comprising (a) a compound of claim 1, wherein Z=S, Y=N, $R^1$=H, and (b) a pharmaceutically acceptable carrier.

25. An in vivo method for detecting amyloid deposits in a subject, comprising the steps of:
(a) administering a detectable quantity of the pharmaceutical composition of claim 23, and
(b) detecting the binding of the compound to amyloid deposit in the subject.

26. The method of claim 25, wherein the amyloid deposit is located in the brain of a subject.

27. The method of claim 25, wherein the subject is suspected of having a disease or syndrome selected from the group consisting of Alzheimer's Disease, familial Alzheimer's Disease, Down's Syndrome and homozygotes for the apolipoprotein E4 allele.

28. The method of claim 25, wherein the detecting is selected from the group consisting of gamma imaging, magnetic resonance imaging and magnetic resonance spectroscopy.

29. The method of claim 28, wherein the detecting is done by gamma imaging, and the gamma imaging is either PET or SPECT.

30. The method of claim 25, wherein the pharmaceutical composition is administered by intravenous injection.

31. The method of claim 25, wherein the ratio of (i) binding of the compound to a brain area other than the cerebellum to (ii) binding of the compound to the cerebellum, in the subject, is compared to the ratio in normal subjects.

32. A method of detecting amyloid deposits in biopsy or post-mortem human or animal tissue comprising the steps of:
(a) incubating formalin-fixed or fresh-frozen tissue with a solution of a compound of claim 1 to form a labeled deposit and then,
(b) detecting the labeled deposits.

33. The method of claim 32 wherein the solution is composed of 25-100% ethanol, with the remainder of the solution being water, wherein the solution is saturated with an amyloid binding compound of the following formula or a water soluble, non-toxic salt thereof:

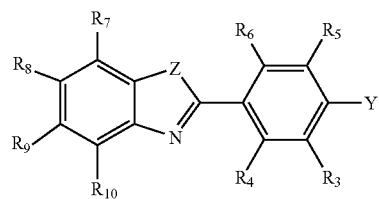

wherein
Z is S, NR', O or CR'
wherein when Z is CR', then the correct tautomeric form of the heterocyclic ring containing Z and N is an indole in which R' is H or a lower alkyl group:

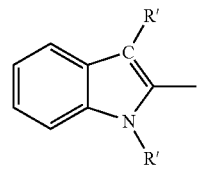

Y is $NR^1R^2$, $OR^2$, or $SR^2$;
wherein the nitrogen of

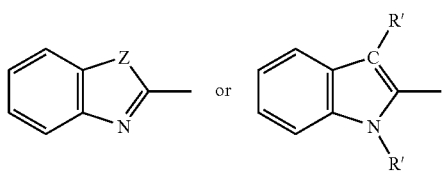

is not a quaternary amine;
each $R^1$ and $R^2$ independently is selected from the group consisting of H, a lower alkyl group, $(CH_2)_nOR'$ (wherein n=1, 2, or 3), $CF_3$, $CH_2$—$CH_2X$, $CH_2$—$CH_2$—$CH_2X$ (wherein X=F, Cl, Br or I), (C=O)—R', $R_{ph}$, and $(CH_2)_nR_{ph}$ (wherein n=1, 2, 3, or 4 and $R_{ph}$ represents an unsubstituted or substituted phenyl group, wherein substituents of $R_{ph}$ are selected from the group consisting of F, Cl, Br, I, a lower alkyl group, $(CH_2)_n$OR' (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', N(R')$_2$, $NO_2$, (C=O)N(R')$_2$, O(CO)R', OR', SR', COOR', (wherein R' is H or a lower alkyl group), a tri-alkyl tin and a chelating group (with or without a chelated metal group) of the form W-L or V-W-L, wherein V is selected from the group consisting of —COO—, —CO—, —$CH_2O$— and —$CH_2NH$—; W is —$(CH_2)_n$ where n=0,1,2,3,4, or 5; and L is:

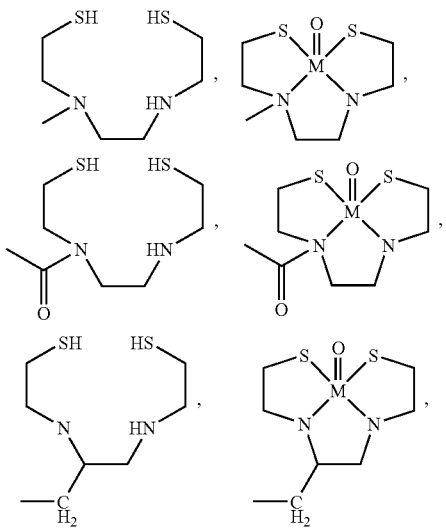

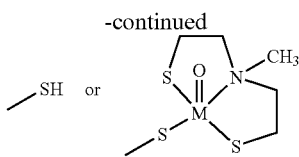

wherein M is selected from the group consisting of Tc and Re;

and R' is H or a lower alkyl group;

each $R^3$-$R^{10}$ are independently is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$, —$CR_2'$—$R_{ph}$ (wherein $R_{ph}$ represents an unsubstituted or substituted phenyl group wherein R' is H or a lower alkyl group), a tri-alkyl tin and a chelating group (with or without a chelated metal group) of the form W-L or V-W-L, wherein V is selected from the group consisting of —COO—, —CO—, —$CH_2O$— and —$CH_2NH$—; W is —$(CH_2)_n$ where n=0,1,2,3,4, or 5; and L is:

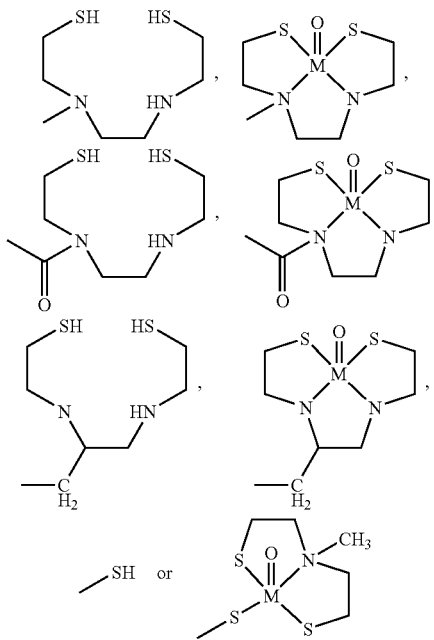

wherein M is selected from the group consisting of Tc and Re;

or each $R^1$ and $R^2$ is a chelating group (without a chelated metal group) of the form W-L wherein W is —$(CH_2)_n$ where N=2,3,4, or 5; and L is:

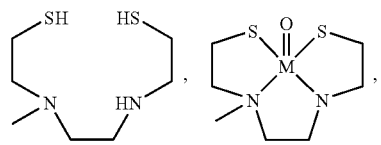

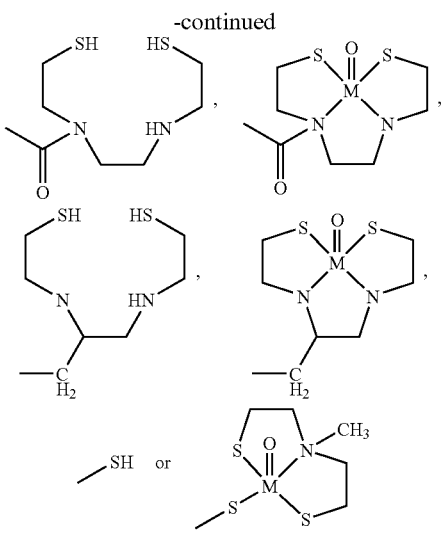

wherein M is selected from the group consisting of Tc and Re;

or wherein each $R^3$-$R^{10}$ independently is selected from the group consisting of a chelating group (with or without a chelated metal ion) of the form W-L and V-W-L, wherein V is selected from the group consisting of —COO—, and —CO—; W is —$(CH_2)_n$ where n=0,1, 2,3,4, or 5; L is:

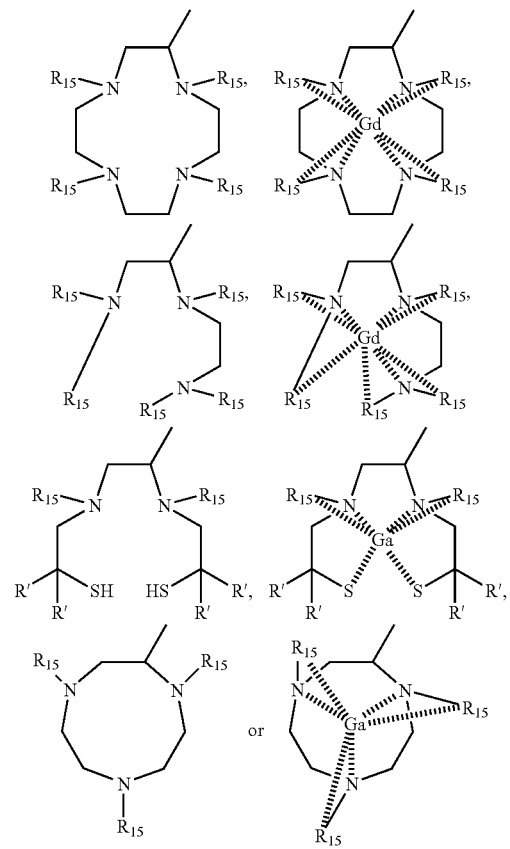

and wherein $R^{15}$ independently is selected from the following:

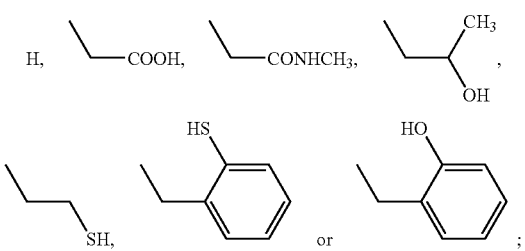

or an amyloid binding, chelating compound (with or without a chelated metal group) or a water soluble, non-toxic salt thereof of the form:

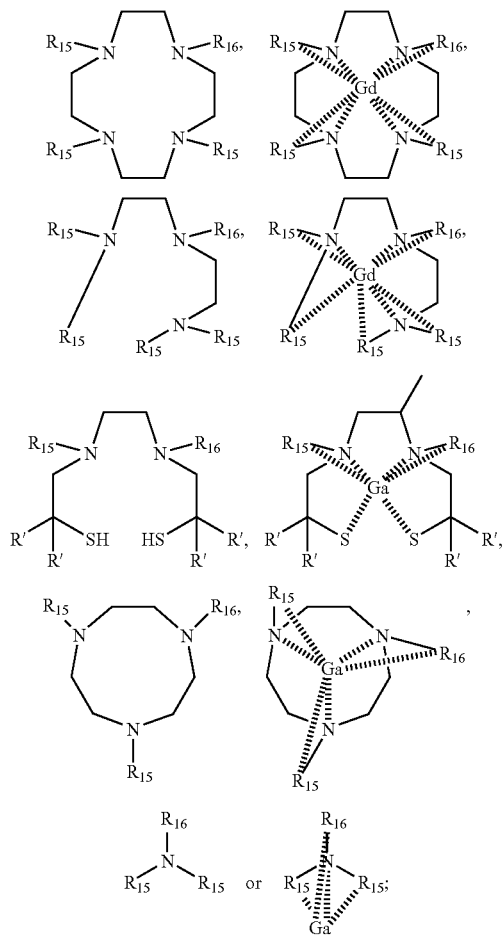

wherein $R^{15}$ independently is selected from the following:

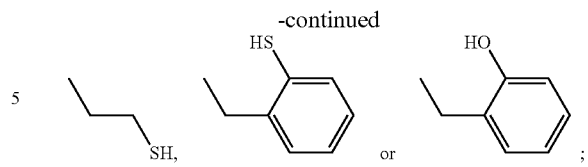

and $R^{16}$ is

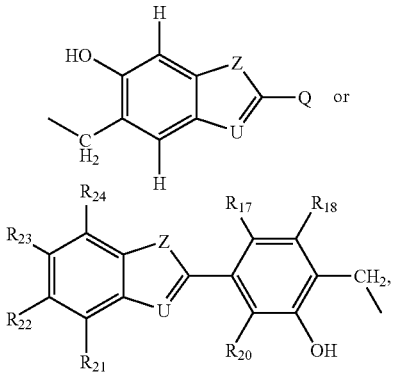

wherein Q is independently selected from one of the following structures:

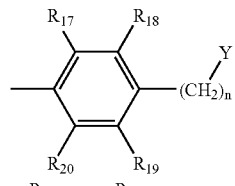  wherein n = 0, 1, 2, 3 or 4,

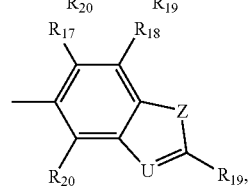 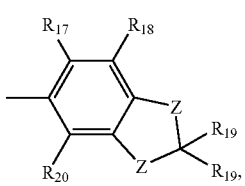

Z is S, NR', O, or C(R')$_2$ in which R' is H or a lower alkyl group;
U is N or CR';
Y is NR$^1$R$^2$, OR$^2$, or SR$^2$;
each $R^{17}$—$R^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group and wherein R' is H or a lower alkyl group);
wherein at least one of the substituents $R^1$-$R^{10}$ is selected from the group consisting of $^3$H, $^{131}$I, $^{125}$I, $^{123}$I, $^{76}$Br, $^{75}$Br, $^{18}$F, CH$_2$—CH$_2$—X*, O—CH$_2$—CH$_2$—X*, CH$_2$—CH$_2$—CH$_2$—X*, O—CH$_2$—

CH$_2$—CH$_2$—X* (wherein X*=$^{131}$I, $^{123}$I, $^{76}$Br, $^{75}$Br or $^{18}$F), $^{19}$F, $^{125}$I, a carbon-containing substituent selected from the group consisting of lower alkyl, (CH$_2$)$_n$OR', CF$_3$, CH$_2$—CH$_2$X, O—CH$_2$—CH$_2$X, CH$_2$—CH$_2$—CH$_2$X, O—CH$_2$—CH$_2$X (wherein X=F, Cl, Br or I), CN, (C=O)—R', (C=O)N(R')$_2$, O(CO)R', COOR', CR'=CR'—R$_{ph}$ and CR$_2$'—CR$_2$'—R$_{ph}$ wherein at least one carbon is $^{11}$C, $^{13}$C or $^{14}$C and a chelating group (with chelated metal group) of the form W-L* or V-W-L*, wherein V is selected from the group consisting of —COO—, —CO—, —CH$_2$O— and —CH$_2$NH—; W is —CH$_2$), where n=0,1,2,3,4, or 5; and L* is:

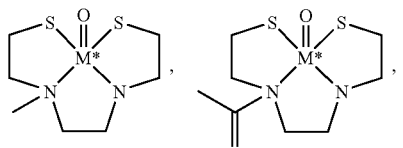

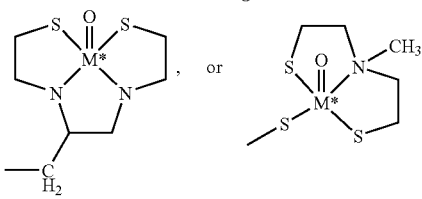

wherein M* is $^{99m}$Tc;
or L* is:

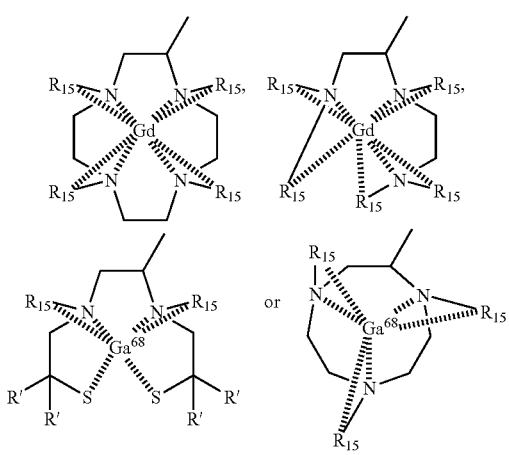

and wherein R$^{15}$ independently is selected from the following:

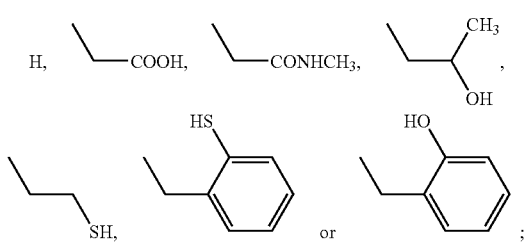

or a chelating compound (with chelated metal group) of the form:

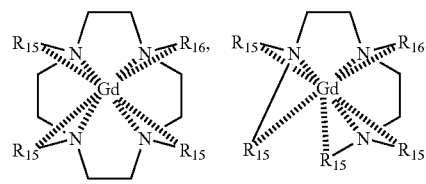

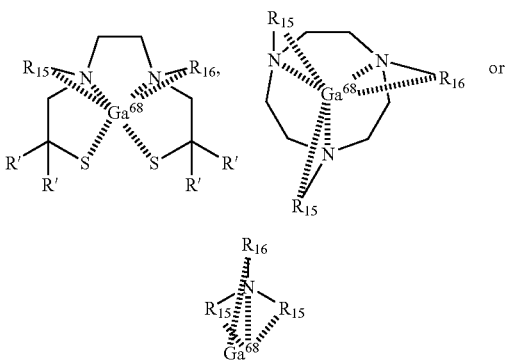

wherein R$^{15}$ independently is selected from the following:

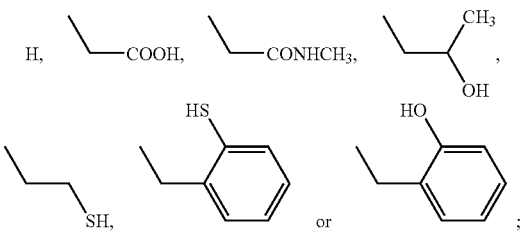

and R$^{16}$ is

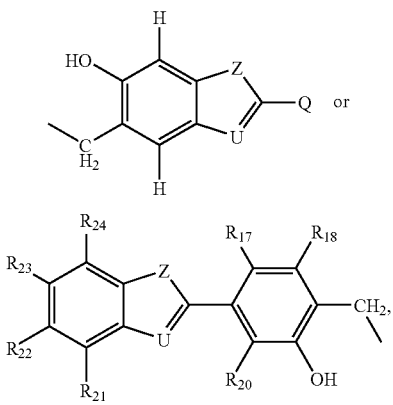

wherein Q is independently selected from one of the following structures:

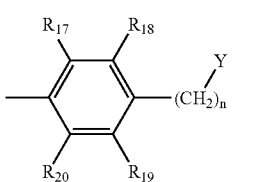  wherein n = 0, 1, 2, 3 or 4,

-continued

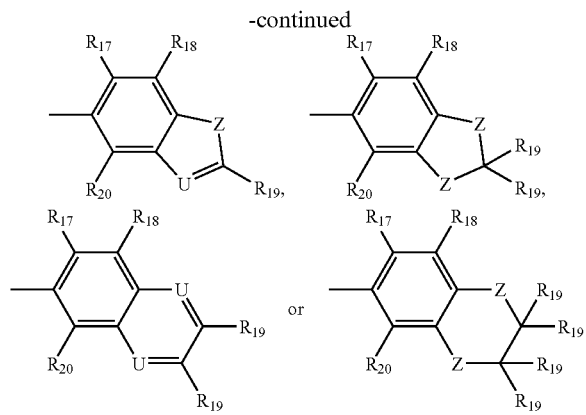

Z is S, NR', O, or C(R')$_2$ in which R' is H or a lower alkyl group;
U is N or CR';
Y is NR$^1$R$^2$, OR$^2$, or SR$^2$;
wherein each R$^{17}$-R$^{24}$ independently is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$ and CR$_2$'—CR$_2$'—R$_{ph}$ (wherein R$_{ph}$ represents an unsubstituted or substituted phenyl group and wherein R' is H or a lower alkyl group).

34. The method of claim 32 wherein the solution is composed of an aqueous buffer containing 0-50% ethanol, wherein the solution contains 0.0001 to 100 μM of the amyloid binding compound.

35. The method of claim 32 wherein the detecting is effected by microscopic techniques selected from the group consisting of bright-field, fluorescence, laser-confocal, and cross-polarization microscopy.

36. A method of quantifying the amount of amyloid in biopsy or post-mortem tissue comprising the steps of:
a) incubating a radiolabeled compound of claim 1 with a homogenate of biopsy or post-mortem tissue, wherein at least one of the substituents R$^1$-R$^{10}$ of the compound is labeled with a radiolabel selected from the group consisting of $^{125}$I, $^3$H, and a carbon-containing substituent as specified in claim 1, wherein at least one carbon is $^{14}$C,
b) separating the tissue-bound from the tissue-unbound radiolabeled compound of claim 1,
c) quantifying the tissue-bound radiolabeled compound of claim 1, and
d) converting the units of tissue-bound radiolabeled compound of claim 1 to units of micrograms of amyloid per 100 mg of tissue by comparison with a standard.

* * * * *